US010550356B2

(12) United States Patent
VanBlarcom et al.

(10) Patent No.: US 10,550,356 B2
(45) Date of Patent: Feb. 4, 2020

(54) SOLID AND LIQUID TEXTILE-TREATING COMPOSITIONS

(75) Inventors: David VanBlarcom, Trumbull, CT (US); Makarand S. Shevade, Plainsboro, NJ (US); Alla Tartakovsky, Monroe, CT (US); Ewa U. Sidwa, Stamford, CT (US)

(73) Assignee: Henkel IP & Holding GmbH (DE)

( * ) Notice: Subject to any disclaimer, the term of this patent is extended or adjusted under 35 U.S.C. 154(b) by 338 days.

(21) Appl. No.: 13/605,866

(22) Filed: Sep. 6, 2012

(65) Prior Publication Data
US 2013/0095717 A1 Apr. 18, 2013

Related U.S. Application Data

(60) Provisional application No. 61/531,540, filed on Sep. 6, 2011, provisional application No. 61/598,831, filed on Feb. 14, 2012.

(51) Int. Cl.
*C11D 3/50* (2006.01)
*G01N 21/78* (2006.01)
(Continued)

(52) U.S. Cl.
CPC ............ *C11D 3/001* (2013.01); *B65D 85/808* (2013.01); *C11D 1/62* (2013.01); *C11D 3/0015* (2013.01);
(Continued)

(58) Field of Classification Search
CPC . C11D 17/041–045; C11D 3/40; C11D 3/502; C11D 1/62; C11D 7/3245;
(Continued)

(56) References Cited

U.S. PATENT DOCUMENTS 3,174,825 A * 3/1965 Birchall ................... 423/268
3,218,776 A 11/1965 Cloud
(Continued)

FOREIGN PATENT DOCUMENTS

DE  2034562 A1 * 1/1972 ............ A61K 8/362
WO  WO 92/01037  1/1991
(Continued)

OTHER PUBLICATIONS

Dreja, WO 2011029772 A1 (Machine TranIsation),Mar. 2011, DE, C11D3/2079.*
(Continued)

*Primary Examiner* — Gerard Higgins
*Assistant Examiner* — Kevin C Ortman, Jr.
(74) *Attorney, Agent, or Firm* — Bojuan Deng

(57) ABSTRACT

Provided herein are solid textile treating compositions; compositions containing colorants stabilized with one or more colorant stabilizers; compositions containing colorants that do not need to be stabilized by one or more colorant stabilizers; solid wash cycle conditioning agents; liquid textile treating compositions; cleaning agent compositions containing these; methods of making these; methods of treating textiles with these; textiles treated by these; containers containing the compositions; and methods of visually designating when a composition has reached or passed its pull date.

17 Claims, 1 Drawing Sheet
(1 of 1 Drawing Sheet(s) Filed in Color)

(51) Int. Cl.

| | | |
|---|---|---|
| *B65D 85/808* | (2006.01) | |
| *C11D 3/00* | (2006.01) | |
| *C11D 3/40* | (2006.01) | |
| *C11D 17/00* | (2006.01) | |
| *C11D 1/62* | (2006.01) | |
| *C11D 3/04* | (2006.01) | |
| *C11D 3/08* | (2006.01) | |
| *C11D 3/10* | (2006.01) | |
| *C11D 3/12* | (2006.01) | |
| *C11D 3/20* | (2006.01) | |
| *C11D 3/22* | (2006.01) | |
| *C11D 3/33* | (2006.01) | |
| *C11D 3/37* | (2006.01) | |
| *C11D 7/10* | (2006.01) | |
| *C11D 7/12* | (2006.01) | |
| *C11D 7/14* | (2006.01) | |
| *C11D 7/26* | (2006.01) | |
| *C11D 7/32* | (2006.01) | |
| *C11D 17/04* | (2006.01) | |
| *C11D 17/06* | (2006.01) | |

(52) U.S. Cl.
CPC ............. *C11D 3/046* (2013.01); *C11D 3/08* (2013.01); *C11D 3/10* (2013.01); *C11D 3/1253* (2013.01); *C11D 3/2075* (2013.01); *C11D 3/2079* (2013.01); *C11D 3/2086* (2013.01); *C11D 3/221* (2013.01); *C11D 3/33* (2013.01); *C11D 3/373* (2013.01); *C11D 3/3707* (2013.01); *C11D 3/3715* (2013.01); *C11D 3/3723* (2013.01); *C11D 3/3753* (2013.01); *C11D 3/3769* (2013.01); *C11D 3/40* (2013.01); *C11D 3/50* (2013.01); *C11D 3/502* (2013.01); *C11D 3/505* (2013.01); *C11D 7/10* (2013.01); *C11D 7/12* (2013.01); *C11D 7/14* (2013.01); *C11D 7/265* (2013.01); *C11D 7/3245* (2013.01); *C11D 17/0039* (2013.01); *C11D 17/0047* (2013.01); *C11D 17/044* (2013.01); *C11D 17/06* (2013.01); *G01N 21/78* (2013.01); *Y10T 442/2303* (2015.04); *Y10T 442/2352* (2015.04)

(58) Field of Classification Search
CPC ....... C11D 3/3715; C11D 3/3769; C11D 3/33; C11D 3/3723; C11D 3/1253; C11D 7/10; C11D 3/221; C11D 3/3707; C11D 7/14; C11D 3/046; C11D 7/265; C11D 7/12; G01N 21/78; Y10T 428/1352
USPC .......... 442/96; 510/523, 327, 515; 427/212; 428/402
See application file for complete search history.

(56) References Cited

U.S. PATENT DOCUMENTS

| | | | | |
|---|---|---|---|---|
| 3,277,009 | A * | 10/1966 | Freifeld et al. ............. | 427/391 |
| 3,322,674 | A * | 5/1967 | Friedman ................... | 510/296 |
| 3,453,779 | A | 7/1969 | Reifenberg | |
| 4,536,418 | A * | 8/1985 | Goldsmith ................ | B01J 8/36 |
| | | | | 427/213 |
| 4,776,455 | A | 10/1988 | Anderson et al. | |
| 4,818,421 | A * | 4/1989 | Boris et al. ................. | 510/297 |
| 4,911,858 | A * | 3/1990 | Bunczk et al. ............. | 510/193 |
| 5,234,615 | A * | 8/1993 | Gladfelter et al. .......... | 510/439 |
| 5,699,653 | A | 12/1997 | Hartman et al. | |
| 5,722,217 | A | 3/1998 | Cloud | |
| 6,025,319 | A | 2/2000 | Surutzidis et al. | |
| 6,037,319 | A | 3/2000 | Dickler et al. | |
| 6,056,949 | A | 5/2000 | Menzi et al. | |
| 6,358,902 | B1 * | 3/2002 | Angell ................. | C11D 3/2079 |
| | | | | 510/295 |
| 6,495,505 | B1 | 12/2002 | Reul et al. | |
| 6,727,215 | B2 | 4/2004 | Roberts et al. | |
| 6,797,685 | B2 * | 9/2004 | Zhu et al. .................... | 510/417 |
| 6,878,679 | B2 | 4/2005 | Sommerville-Roberts et al. | |
| 7,259,134 | B2 | 8/2007 | Beckholt et al. | |
| 7,282,472 | B2 | 10/2007 | Kapur et al. | |
| 7,304,025 | B2 | 12/2007 | Hardy et al. | |
| 7,329,441 | B2 | 2/2008 | Catlin et al. | |
| 7,439,215 | B2 | 10/2008 | Catlin et al. | |
| 7,446,084 | B2 * | 11/2008 | Barthel et al. .............. | 510/296 |
| 7,464,519 | B2 | 12/2008 | Fisher et al. | |
| 7,528,099 | B2 * | 5/2009 | Wahl et al. .................. | 510/295 |
| 7,595,290 | B2 | 9/2009 | Pounds et al. | |
| 7,727,946 | B2 * | 6/2010 | Catalfamo et al. .......... | 510/296 |
| 7,871,976 | B1 | 1/2011 | Aouad | |
| 2001/0046607 | A1 | 11/2001 | White et al. | |
| 2002/0013242 | A1 * | 1/2002 | Baillely et al. ............. | 510/220 |
| 2004/0004206 | A1 | 1/2004 | Kelley et al. | |
| 2005/0020476 | A1 | 1/2005 | Wahl et al. | |
| 2006/0019859 | A1 | 1/2006 | Duran et al. | |
| 2006/0094097 | A1 * | 5/2006 | Becker et al. .............. | 435/182 |
| 2006/0216424 | A1 * | 9/2006 | Maurer et al. ............ | 427/376.1 |
| 2006/0217288 | A1 | 9/2006 | Wahl et al. | |
| 2006/0257596 | A1 * | 11/2006 | Catalfamo ................ | A23F 5/36 |
| | | | | 428/34.1 |
| 2006/0287215 | A1 | 12/2006 | McDonald et al. | |
| 2007/0049511 | A1 * | 3/2007 | Lawshe ............... | C11D 3/2079 |
| | | | | 510/424 |
| 2009/0032063 | A1 * | 2/2009 | Haas ....................... | C11D 3/10 |
| | | | | 134/18 |
| 2009/0042766 | A1 * | 2/2009 | Mayer .................... | C11D 3/001 |
| | | | | 510/516 |
| 2009/0082244 | A1 | 3/2009 | Mayer et al. | |
| 2009/0197765 | A1 * | 8/2009 | Gaytan et al. .............. | 504/130 |
| 2010/0069284 | A1 * | 3/2010 | Prabhat et al. .............. | 510/355 |
| 2010/0113616 | A1 | 5/2010 | Gerke et al. | |
| 2011/0082066 | A1 * | 4/2011 | Wrubbel et al. ............ | 510/327 |
| 2012/0108487 | A1 | 5/2012 | Graham et al. | |
| 2012/0165239 | A1 * | 6/2012 | Dreja ..................... | C11D 3/2079 |
| | | | | 510/299 |
| 2012/0302489 | A1 * | 11/2012 | Rodrigues et al. .......... | 510/439 |
| 2013/0196892 | A1 * | 8/2013 | Bonsall et al. .............. | 510/439 |

FOREIGN PATENT DOCUMENTS

| | | | | |
|---|---|---|---|---|
| WO | WO 94/10285 | | 5/1994 | |
| WO | WO 95/08617 | | 3/1995 | |
| WO | WO-0242408 A2 * | | 5/2002 | ............ B65B 9/042 |
| WO | WO 2010000636 A1 * | | 1/2010 | ............ C11D 3/00 |
| WO | WO 2011029772 A1 * | | 3/2011 | ........... C11D 3/2079 |

OTHER PUBLICATIONS

Library of Congress ("Everyday Mysteries," p. 1-2, https://www.loc.gov/rr/scitech/mysteries/colors.html, accessed Aug. 29, 2017). (Year: 2017).*

Henkel( DE-2034562A1 machine translation, p. 1-4, 1972). (Year: 1972).*

International Search Report and Written Opinion for International Application No. PCT/US2012/053993, United States Patent and Trademark Office, United States, dated Jan. 17, 2013.

Davies, J.T., "A Quantitative Kinetic Theory of Emulsion Type, 1. Physical Chemistry of the Emulsifying Agent," in *Gas/Liquid and Liquid/Liquid Interface* pp. 426-438, Proceedings of the 2$^{nd}$ International Congress of Surface Activity, Butterworths, London (1957).

Griffin, W. C., "Classification of Surface-Active Agents by 'HLB'," *Journal of the Society of Cosmetic Chemists* 1:311-326, Oxford, England (1949).

Supplementary European Search Report and Search Opinion for the European Application EP 12829851.0, European patent office, Germany, dated May 15, 2015.

* cited by examiner

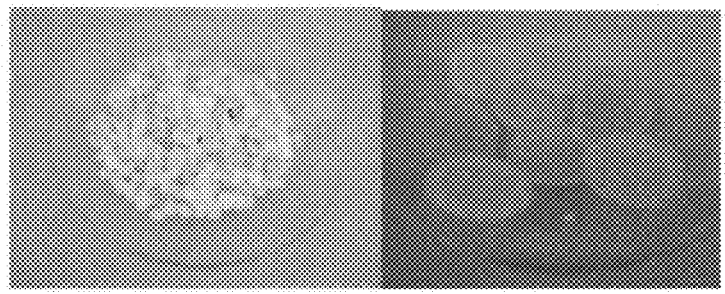

SOLID AND LIQUID TEXTILE-TREATING COMPOSITIONS

CROSS-REFERENCE TO RELATED APPLICATIONS

The present application claims the benefit of the filing dates of U.S. Provisional Application No. 61,531,540, filed Sep. 6, 2011, and U.S. Provisional Application No. 61/598,831, filed Feb. 14, 2012, the disclosures of both of which are incorporated by reference herein in their entireties.

BACKGROUND OF THE INVENTION

Field of the Invention

This application relates to solid or liquid textile-treating compositions, as well as their use and manufacture. The application also relates to cleaning agent compositions employing solid or liquid textile-treating compositions, and their use and manufacture.

Description of the Related Art

Textiles can become hard due to repeated washings. Also, after washing, textiles can have an undesirable smell. To restore their softness, improve their scent, or impart other desirable properties, textiles are often treated by additional processes that are separate from their washing. The treatments are separate because the textile-treating compositions are often not compatible with the washing detergent. These additional processes can be done, for example, in the washer during an added rinse cycle, or in the dryer. However, separate treatments have drawbacks. For example, when a textile is treated with a liquid fabric softener, an additional rinse cycle may be needed, which uses extra water and electricity to power the washer. The use of extra water and electricity can be detrimental to the environment. Also, some separate treatments employ liquid compositions such as liquid fabric softeners. These liquid compositions contain excess weight and have excess volume imparted by an inert ingredient: water. The water in the liquid compositions makes liquid compositions expensive to transport and can generate excess container waste.

United States Patent Application Publication No. 2009/0082244 ("the '244 application") relates to a solid, textile or skin care composition which comprises a water-soluble carrier, a textile-softening clay and a textile or skin care compound. The compositions of the '244 application can contain colorants. Preferred colorants are alleged to possess high storage stability, are not affected by other composition ingredients, and do not color treated textiles.

United States Patent Application Publication No. 2009/0042766 ("the '766 application") relates to solid, textile care compositions having a water-soluble carrier, a textile care compound, and a perfume. The solid, textile care compositions can be present in particulate form, and can be included in washing or cleaning compositions. The compositions of the '766 application can contain pigments or dyes. Preferred dyes are alleged to possess high storage stability, are insensitive to other composition ingredients and light, and do not color treated textiles.

United States Patent Application Publication No. 2011/0082066 ("the '066 application") is drawn to solid fabric care compositions comprising a water-soluble carrier, a water-soluble, polymer a fabric care compound, a polysaccharide and a fragrance. The water-soluble carrier is in particle form and is coated, with the polysaccharide being incorporated at least partly into the coating. The solid fabric care compositions can be included in washing or cleaning products. The solid fabric care compositions of the '066 application can be colored. The '066 application discloses that " . . . cellulose or its derivatives increase the color stability of colored solid fabric care compositions."

Thus, there remains a need for solid, textile-treating compositions that can be employed in the presence of a detergent while textiles are washed.

BRIEF SUMMARY OF THE INVENTION

The compositions, containers containing the compositions, methods, and treated textiles provided are exemplary and are not intended to limit the scope of the claimed embodiments.

One aspect of the claimed embodiments is the use of colorant stabilizer(s) to stabilize colorant(s) in a solid or liquid composition. As described herein, it has been discovered that colorants widely thought to be stable were in fact unstable in solid, particulate compositions such as solid, textile-treating compositions ("STTCs"), and unstable in liquid compositions. The present inventors found that colorant stabilizers, that were not celluloses or cellulose derivatives, can be employed to stabilize colorants in solid, particulate compositions such as STTCs, and also in liquid compositions. It has also been discovered that in solid compositions, particulate compositions, and in liquid compositions, faded colorants could be "re-colorized" by the addition of colorant stabilizers that were not celluloses or cellulose derivatives.

In one embodiment is provided a solid, textile-treating composition ("STTC"). The STTC comprises a core, a coating that at least partially surrounds the core, and a flow aid physically associated with the coating such that the flow aid is partially or fully exposed on an outer surface of the coating. The core can comprise a carrier, which can be a water-soluble carrier. The core can be water-soluble. The coating can comprise a water-soluble polymer, a colorant, and a colorant stabilizer. The coating can also comprise a perfume (which may also be referred to herein, interchangeably and equivalently, as a fragrance). The flow aid can comprise a fabric softener.

Cores, water-soluble cores, carriers, water-soluble carriers, or STTCs can be particles. The particles can be free-flowing. The particles can be small. Thus, STTCs can be free-flowing small particles.

In a further embodiment is provided a cleaning agent composition comprising a detergent and an STTC. The detergent can comprise a surfactant.

Another provided embodiment is a container containing the cleaning agent composition or the STTC. Such containers can include, but are not limited to, pouches or other container forms comprising or made from thin films, such as polyvinylalcohol (PVOH) films. In certain such embodiments, the container containing the cleaning agent composition or the STTC can be in the form of a single-dose package suitable for addition to the washing machine at the beginning of the wash cycle.

A further embodiment is a method of perfuming a textile with an STTC.

Another embodiment is a method of softening a textile with an STTC.

Another embodiment is a method of perfuming a textile, e.g., delivering a fragrance to a textile, with an STTC.

Yet another embodiment is a method of perfuming and softening a textile with an STTC.

An additional embodiment is a method of cleaning a textile with a cleaning agent composition.

Another embodiment is a textile cleaned or perfumed or softened by an STTC.

An additional embodiment is a textile cleaned with a cleaning agent composition.

A further embodiment is a method of stabilizing a colorant in a granular composition, or in a solid composition, or in a liquid composition, where the colorant is stabilized by incorporating a colorant stabilizer in the composition.

Another embodiment is a method of visually designating when a granular composition, or a solid composition, or a liquid composition, has reached or passed its pull date by determining whether or when the composition becomes substantially colorless.

An additional embodiment includes a method of making a cleaning agent composition comprising blending a detergent with an STTC, a solid composition, a liquid composition, or a granular composition.

A further embodiment includes a method of making an STTC comprising at least partially coating a core to form a coated core and applying a flow aid to the at least partially coated core to form the STTC.

Another embodiment includes cleaning agent compositions or STTCs made by these methods.

A further embodiment is a solid textile-treating composition ("STTC"), comprising:
a water-soluble core comprising a water-soluble carrier:
a coating that at least partially covers the water-soluble core, the coating comprising
a water-soluble polymer;
a colorant selected from the group consisting of Acid Blue 80, Acid Red 52, Acid Violet 48, and combinations thereof; and
a flow aid physically associated with the coating such that the flow aid is partially or fully exposed on an outer surface of the coating; wherein the composition does not contain a colorant stabilizer. Surprisingly, it has been found that Acid Blue 80, Acid Red 52, and Acid Violet 48, do not display significant discoloration over time in STTCs and thereby do not require a colorant stabilizer.

A further embodiment includes a solid wash cycle conditioning agent ("SWCCA") that includes: a) a non-ionic surfactant, which can be an EO/PO block copolymer, or a polysorbate, or a combination of these materials, wherein the non-ionic surfactant is a solid at about 25° C., wherein the non-ionic surfactant can have an HLB value of about 20 or more, and wherein the non-ionic surfactant can have a weight average molecular weight ranging from about 3,000 to about 12,000; and b) a fabric conditioning agent which can be, for example, a quaternary ammonium salt. The SWCCA can optionally include one or more plasticizers; one or more colorants; one or more colorant stabilizers; and/or one or more perfumes. It has been surprisingly found that solid wash cycle conditioning agents possess the ability to dissolve in cold water in a laundry wash cycle. Depending on the particle size of the SWCCA, the SWCCA may also optionally include a disintegrating agent, for example, as the particle size increases. The SWCCA can take a variety of shapes including pastilles, crystals, powders, pulverized powders, spray dried powders, agglomerated powders, checkers, round discs and tablets.

Another embodiment includes methods of making SWCCAs.

An additional embodiment includes methods of treating textiles with SWCCAs.

A further embodiment includes SWCCAs in the form of unit doses.

A further embodiment includes unit doses.

An additional embodiment includes a liquid textile treating composition ("LTTC"). The LTTC includes: a) one or more polyethylene glycols; b) one or more alcohols, that can be, for example, polyols; c) water; d) a fabric conditioning agent which can be, for example, a quaternary ammonium salt. The LTTC can optionally include one or more colorants; one or more colorant stabilizers; and/or one or more perfumes.

A further embodiment includes methods of making LTTCs.

Another embodiment includes methods of treating textiles with LTTCs.

BRIEF DESCRIPTION OF THE FIGURE

The patent or application file contains at least one drawing executed in color. Copies of this patent or patent application publication with color drawing(s) will be provided by the Office upon request and payment of necessary fee.

FIG. 1 shows inventive embodiments in different physical forms.

DETAILED DESCRIPTION OF THE INVENTION

Definitions

All of the various aspects, embodiments, and options disclosed herein can be combined in any and all variants unless otherwise specified.

As used herein, "a" means one or more unless otherwise specified.

Open terms such as "include," "including," "contain," "containing" and the like mean "comprising."

The act of treating a textile can refer to, for example, one or more of: i) applying a perfume to a textile; ii) softening a textile; iii) applying a perfume to and softening a textile; iv) cleaning a textile; v) rendering the textile resistant to static build up during drying; or vi) cleaning a textile and applying a perfume to and softening a textile and rendering the textile resistant to static build up during drying; or any combination thereof.

Terms in this application control in the event of a conflict with a patent or publication term that is incorporated by reference.

The term "or" can be conjunctive or disjunctive.

Some inventive embodiments contemplate numerical ranges. Every numerical range provided herein includes the range endpoints as individual inventive embodiments. When a numerical range is provided, all individual values and subranges therein are present as if explicitly written out.

The term "substantially colorless" means that a colorant in an STTC or granular composition has lost most its ability to color the STTC or composition such that the STTC or composition appears to be predominantly the color of its core or coating or flow aid or ingredients.

The term "colorless" means that a colorant in an STTC or granular composition has lost its ability to color the STTC or composition such that the STTC or composition appears to be the color of its core or coating or flow aid or ingredients.

The term "pull date" means the expiration date of a product.

Discussion

Solid Textile-Treating Compositions

In one embodiment, provided is a solid textile-treating composition ("STTC"). The STTC can be used, for example, to treat a textile.

In one embodiment, the STTC has a core that incorporates a carrier; a coating that at least partially covers the core; and a flow aid physically associated with the coating such that the flow aid is partially or fully exposed on an outer surface of the coating. The carrier or the core can be water-soluble. The coating includes a water-soluble polymer, a colorant, and a colorant stabilizer. The coating can further incorporate a perfume. The flow aid can include a fabric softener. And the STTC can further include additives.

The core or water-soluble core can contain ingredients or materials other than the carrier or water-soluble carrier. Alternatively, the core or water-soluble core can be the carrier or water-soluble carrier.

The STTC, in one embodiment, does not include a cellulose, a polysaccharide, alginic acid, algenic acid, or any combination thereof.

In one embodiment, the STTC does not comprise a fabric softener.

Cores, water-soluble cores, carriers, water-soluble carriers, or STTCs can be particles. The particles can be free-flowing. The particles can be small. Thus, an STTC can be a free-flowing small particle.

Cores and Carriers

A core may contain one or more carriers. The carrier can be, for example, an inorganic alkali metal salt, an inorganic alkaline earth metal salt, an organic alkali metal salt, an organic alkaline earth metal salt, a carbohydrate, a silicate, a urea, or any combination thereof.

Desirable carrier materials may be fully water-soluble.

Thus, in one embodiment, the core is a water-soluble core that comprises a water-soluble carrier. In other embodiments, the core is a water-soluble core that consists of a water-soluble carrier. In this case, the water-soluble core is the water-soluble carrier.

On the other hand, some desirable carriers may be water-insoluble or only partially water-soluble. Thus, in some embodiments, the core may comprise or consist of partially water-soluble carriers or water-insoluble carriers.

The water-soluble carrier can be, for example, a water-soluble inorganic alkali metal salt, a water-soluble alkaline earth metal salt, a water-soluble organic alkali metal salt, a water-soluble organic alkaline earth metal salt, a water-soluble carbohydrate, a water-soluble silicate, a water-soluble urea, or any combination thereof.

Alkali metal salts can be, for example, salts of lithium, sodium, potassium, rubidium, cesium, francium, or any combination thereof.

Useful alkali metal salts can be, for example, alkali metal fluorides, chlorides, bromides, iodides, sulfates, bisulfates, phosphates, monohydrogen phosphates, dihydrogen phosphates, carbonates, monohydrogen carbonates, acetates, citrates, lactates, pyruvates, silicates, ascorbates, or any combination thereof.

Alkali metal salts can include, for example, sodium fluoride, sodium chloride, sodium bromide, sodium iodide, sodium sulfate, sodium bisulfate, sodium phosphate, sodium monohydrogen phosphate, sodium dihydrogen phosphate, sodium carbonate, sodium hydrogen carbonate, sodium acetate, sodium citrate, sodium lactate, sodium tartrate, sodium silicate, sodium ascorbate, potassium fluoride, potassium chloride, potassium bromide, potassium iodide, potassium sulfate, potassium bisulfate, potassium phosphate, potassium monohydrogen phosphate, potassium dihydrogen phosphate, potassium carbonate, potassium monohydrogen carbonate, potassium acetate, potassium citrate, potassium lactate, potassium tartrate, potassium silicate, potassium ascorbate, or any combination thereof.

Alkaline earth metal salts include, for example, salts of beryllium, magnesium, calcium, strontium, barium, radium, or any combination thereof.

Alkaline earth metal salts can be, for example, alkaline metal fluorides, chlorides, bromides, iodides, sulfates, bisulfates, phosphates, monohydrogen phosphates, dihydrogen phosphates, carbonates, monohydrogen carbonates, acetates, citrates, lactates, pyruvates, silicates, ascorbates, or any combination thereof.

Alkaline earth metal salts can include, for example, magnesium fluoride, magnesium chloride, magnesium bromide, magnesium iodide, magnesium sulfate, magnesium phosphate, magnesium monohydrogen phosphate, magnesium dihydrogen phosphate, magnesium carbonate, magnesium monohydrogen carbonate, magnesium acetate, magnesium citrate, magnesium lactate, magnesium tartrate, magnesium silicate, magnesium ascorbate, calcium fluoride, calcium chloride, calcium bromide, calcium iodide, calcium sulfate, calcium phosphate, calcium monohydrogen phosphate, calcium dihydrogen phosphate, calcium carbonate, calcium monohydrogen carbonate, calcium acetate, calcium citrate, calcium lactate, calcium tartrate, calcium silicate, calcium ascorbate, or any combination thereof.

Inorganic salts, such as inorganic alkali metal salts and inorganic alkaline earth metal salts, do not contain carbon.

Organic salts, such as organic alkali metal salts and organic alkaline earth metal salts, contain carbon.

In one embodiment, the organic salt can be an alkali metal salt or an alkaline earth metal salt of sorbic acid (i.e., a sorbate). Sorbates can include, for example, sodium sorbate, potassium sorbate, magnesium sorbate, calcium sorbate, or any combination thereof.

The water-soluble carrier can be, for example, a water-soluble inorganic alkali metal salt, a water-soluble organic alkali metal salt, a water-soluble inorganic alkaline earth metal salt, a water-soluble organic alkaline earth metal salt, a water-soluble carbohydrate, a water-soluble silicate, a water-soluble urea, or any combination thereof.

The carrier or water soluble-soluble carrier can be, for example, sodium chloride, potassium chloride, calcium chloride, magnesium chloride, sodium sulfate, potassium sulfate, magnesium sulfate, sodium carbonate, potassium carbonate, sodium hydrogen carbonate, potassium hydrogen carbonate, sodium acetate, potassium acetate, sodium citrate, potassium citrate, sodium tartrate, potassium tartrate, potassium sodium tartrate, calcium lactate, water glass, sodium silicate, potassium silicate, dextrose, fructose, galactose, isoglucose, glucose, sucrose, raffinose, isomalt, xylitol, candy sugar, coarse sugar, or any combination thereof.

In one embodiment, the carrier or water-soluble carrier is sodium chloride.

In one embodiment, the carrier or water-soluble carrier is table salt.

In one embodiment, the carrier or water-soluble carrier is pretzel salt.

In one embodiment, the carrier or water-soluble carrier is Kleer salt.

In one embodiment, the carrier or water-soluble carrier is rock salt.

In one embodiment, the carrier or water-soluble carrier is sea salt.

In one embodiment, the carrier or water-soluble carrier is solar salt with IPS (yellow prussiate of soda) (available from Morton Salt, Inc.; Chicago, Ill.).

In one embodiment, the carrier or water-soluble carrier is a combination of sodium chloride and at least one of magnesium carbonate, potassium idodide, potassium iodidate, or any combination thereof.

In one embodiment, the core is a particle. The coating and the flow aid are then applied to the core to form an STTC that is also a particle. STTCs can thus be a collection of particles. STTCs can be made up of particles where each particle contains the same ingredients. Alternatively, an STTC can be a mixture of two or more distinct STTC particles where each distinct STTC particle has a different ingredient composition. When this is the case, the distinct STTC particles in the STTC composition can differ by one, or two, or three, or more ingredients.

Particle size can be measured across the longest distance (length) of a particle. The particle size can be an average particle size.

The particle size or average particle size can range, for example, from about 0.1 mm to about 50 mm. Particle size can be for example, individually, cores, water-soluble cores, carriers, water-soluble carriers, or STTCs.

The particle size or average particle size can range, for example, from about 0.1 mm to 45 mm, from about 0.1 mm to about 40 mm, about 0.1 mm to about 35 mm, about 0.1 mm to about 30 mm, about 0.1 mm to about 25 mm, about 0.1 mm to about 20 mm, about 0.1 mm to about 15 mm, about 0.1 mm to about 10 mm, or about 0.1 to about 5 mm.

The particle size or average particle size can range, for example, from about 0.5 mm to about 50 mm, from about 1 mm to about 50 mm, about 5 mm to about 50 mm, about 10 mm to about 50 mm, about 15 mm to about 50 mm, about 20 mm to about 50 mm, about 25 mm to about 50 mm, about 30 mm to about 50 mm, about 35 mm to about 50 mm, about 40 mm to about 50 mm, or about 45 mm to about 50 mm.

The particle size or average particle size can range, from example, from about 20 mm to about 30 mm, about 15 mm to about 35 mm, about 10 mm to about 40 mm, or about 5 mm to about 45 mm.

The particle size or average particle size can be, for example, about 0.2 mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, or about 49 mm.

In one embodiment, the STTC, core, water-soluble core, carrier, or water-soluble carrier can, independently, be a nanoparticle. The nanoparticle's particle size or average particle size car, independently, be a positive particle size or average particle size of, for example about 10,000 nm or less, about 9,000 nm or less, about 8,000 nm or less, about 7,000 nm or less, about 6,000 nm or less, about 5,000 nm or less, about 4,000 nm or less, about 3,000 nm or less, about 2,000 nm or less, about 1000 nm or less, about 900 nm or less, about 800 nm or less, about 700 nm or less, about 600 nm or less, about 500 nm or less, about 400 nm or less, about 300 nm or less, about 200 nm or less, about 100 nm or less, about 90 nm or less, about 80 nm or less, about 70 nm or less, about 60 nm or less, about 50 nm or less, about 40 nm or less, about 30 nm or less, about 20 nm or less, about 10 nm or less, about 5 nm or less, or about 1 nm or less.

The nanoparticle's particle size or average particle size can independently be, for example, from about 10,000 nm to about 1 nm, about 9,000 nm to about 1 nm, about 8,000 nm to about 1 nm, about 7,000 nm to about 1 nm, about 6,000 nm to about 1 nm, about 5,000 nm to about 1 nm, about 4,000 nm to about 1 nm, about 3,000 nm to about 1 nm, about 2,000 nm to about 1 nm, about 1,000 nm to about 1 nm, about 900 nm to about 1 nm, about 800 nm to about 1 nm, about 700 nm to about 1 nm, about 600 nm to about 1 nm, about 500 nm to about 1 nm, about 400 nm to about 1 nm, about 300 nm to about 1 nm, about 200 nm to about 1 nm, about 100 nm to about 1 nm, about 90 nm to about 1 nm, about 80 nm to about 1 nm, about 70 nm to about 1 nm, about 60 nm to about 1 nm, about 50 nm to about 1 nm, about 40 nm to about 1 nm, about 30 nm to about 1 nm, about 20 nm to about 1 nm or about 10 nm to about 1 nm.

The nanoparticle's particle size or average particle size can independently be, for example, from about 1 nm to about 10,000 nm, from about 10 nm to about 10,000 nm, from about 20 nm to about 10,000 nm, from about 30 nm to about 10,000 nm, from about 40 nm to about 10,000 nm, from about 50 nm to about 10,000 nm, from about 60 nm to about 10,000 nm, from about 70 nm to about 10,000 nm, from about 80 nm to about 10,000 nm, from about 90 nm to about 10,000 nm, from about 100 nm to about 10,000 nm, from about 200 nm to about 10,000 nm, from about 300 nm to about 10,000 nm, from about 400 nm to about 10,000 nm, from about 500 nm to about 10,000 nm, from about 600 nm to about 10,000 nm, from about 700 nm to about 10,000 nm, from about 800 nm to about 10,000 nm, from about 900 nm to about 10,000 nm, from about 1,000 nm to about 10,000 nm, from about 2,000 to about 10,000 nm, from about 3,000 to about 10,000 nm, from about 4,000 to about 10,000 nm, from about 5,000 nm to about 10,000 nm, from about 6,000 nm to about 10,000 nm, from about 7,000 nm to about 10,000 nm, from about 8,000 nm to about 10,000 nm, or from about 9,000 nm to about 10,000 nm.

The nanoparticle's particle size or average particle size can independently be, for example, about 1 nm, about 10 nm, about 20 nm, about 30 nm, about 40 nm, about 50 nm, about 60 nm, about 70 nm, about 80 nm, about 90 nm, about 100 nm, about 200 nm, about 300 nm, about 400 nm, about 500 nm, about 600 nm, about 700 nm, about 800 nm, about 900 nm, about 1,000 nm, about 2,000 nm, about 3,000 nm, about 4,000 nm, about 5,000 nm, about 6,000 nm, about 7,000 nm, about 8,000 nm, about 9,000 nm, or about 10,000 nm.

The shape of the core, carrier, water-soluble carrier, the water-soluble core, or the STTC individually, is not limited. The shape, individually, can be, for example, cubic, conical, spherical, an oblate spheroid, a prolate spheroid, irregular, fractal, star shaped, box shaped, heart shaped, diamond shaped, club shaped, spade shaped, disc shaped, or any combination thereof.

The core, carrier, water-soluble carrier or water-soluble core can, individually, be crystalline. The crystal can contain, individually, for example, a crystal lattice that is cubic, isometric, tetragonal, orthorhombic, hexagonal, trigonal, triclinic, or monoclinic.

The core, carrier, water-soluble carrier or water-soluble core can comprise, individually, for example, from about 50% by weight to about 95% by weight of the STTC.

The core, carrier, water-soluble carrier or water-soluble core can comprise, individually, for example, about 51% by weight, about 52% by weight, about 53% by weight, about 54% by weight, about 55% by weight, about 56% by weight, about 57% by weight, about 58% by weight, about 59% by weight, about 60% by weight, about 61% by weight, about 62% by weight, about 63% by weight, about 64% by weight, about 65% by weight, about 66% by weight, about 67% by weight, about 68% by weight, about 69% by weight, about 70% by weight, about 71% by weight, about 72% by weight, about 73% by weight, about 74% by weight, about 75% by weight, about 76% by weight, about 77% by weight, about 78% by weight, about 79% by weight, about 80% by weight, about 81% by weight, about 82% by weight, about 83% by weight, about 84% by weight, about 85% by weight, about 86% by weight, about 87% by weight, about 88% by weight, about 89% by weight, about 90% by weight, about 91% by weight, about 92% by weight, about 93% by weight, or about 94% by weight, based on the total weight of the STTC.

Coatings

In one embodiment, the coating comprises a water-soluble polymer, a colorant, and a colorant stabilizer.

In a further embodiment, the coating further comprises a perfume (which is also referred to herein equivalently and interchangeably as, and will also be understood by those of ordinary skill in the art to be equivalent to and interchangeable with, the term "fragrance").

In an additional embodiment, the coating comprises a flow aid.

In another embodiment, at least some coating ingredients are homogeneously mixed.

In a further embodiment, at least some coating ingredients are not homogeneously mixed.

In one embodiment, the coating partially coats the core.

In another embodiment, the coating completely coats the core.

In one embodiment, the water-soluble polymer, colorant, colorant stabilizer and optionally the perfume are homogeneously mixed.

In one embodiment, the water-soluble polymer, the colorant, the colorant stabilizer, and optionally the perfume are not homogeneously mixed.

In a further embodiment, all coating ingredients except the flow aid are homogeneously mixed in the coating.

In another embodiment, the coating further comprises a flow aid.

In a further embodiment, the flow aid is homogenously mixed with the other ingredients in the coating.

In one embodiment, the coating does not comprise a polysaccharide. In one embodiment, the coating does not comprise a cellulose.

In embodiment, the coating does not comprise alginic acid. In one embodiment, the coating does not comprise algenic acid.

United States Patent Application Publication No. 2011/0082066 ("the '066 application") discloses that " . . . cellulose or its derivatives increase the stability of colored solid fabric care compositions." Applicants have found that colorant stabilizers, that are not celluloses or cellulose derivatives, can increase the stability of colored solid fabric care compositions (e.g., STTCs).

Thus, in one embodiment, at least some of the colorant in an STTC or solid composition is stabilized by a colorant stabilizer that is not a polysaccharide, a cellulose, an alginic acid, an algenic acid, or any combination of these. For example, in the coating of an STTC, at least some of the colorant is stabilized by a colorant stabilizer that is not a polysaccharide, a cellulose, an alginic acid, an algenic acid, or any combination of these.

In one embodiment, the coating has a thickness ranging from about 0.0001 mm to about 20 mm. The coating thickness can be an average of the thickest and thinnest portions of the coating added together and divided by two.

For example, the coating thickness can be about 0.0001 mm, about 0.01 mm, about 0.1 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, or about 19 mm.

The coating thickness can range, for example, from about 0.0001 mm to about 18 mm, from about 0.0001 mm to about 16 mm, about 0.0001 mm to about 14 mm, about 0.0001 mm to about 12 mm, about 0.0001 mm to about 10 mm, about 0.0001 mm to about 8 mm, about 0.0001 mm to about 6 mm, about 0.0001 mm to about 4 mm, about 0.0001 mm to about 2 mm, about 0.0001 mm to about 1 mm, about 0.0001 mm to about 0.1 mm, or about 0.0001 mm to about 0.01 mm.

The coating thickness can range, for example, from about 0.01 mm to about 20 mm, about 0.1 mm to about 20 mm, about 1 mm to 20 mm, about 2 mm to about 20 mm, about 4 mm to about 20 mm, about 6 mm to about 20 mm, about 8 mm to about 20 mm, about 10 mm to about 20 mm, about 12 mm to about 20 mm, about 14 mm to about 20 mm, about 16 mm to about 20 mm, or about 18 mm to about 20 mm.

The coating thickness can range, for example, from about 8 mm to about 12 mm, about 7 mm to about 13 mm, about 6 mm to about 14 mm, about 5 mm to about 15 mm, about 4 mm to about 16 mm, about 3 mm to about 17 mm, about 2 mm to about 18 mm, or about 1 mm to about 19 mm.

Water-Soluble Polymers

The water-soluble polymer can have, independently, a melting point temperature or a softening point temperature ranging, for example, from about 45° C. to about 300° C. Melting point temperature refers to the temperature at which the water-soluble polymer transitions from a solid state to liquid (free-flowing) state. Softening point temperature refers to the temperature at which the water-soluble polymer transitions from a solid state to a rubbery to viscous melt. Melting point temperature ranges and softening point temperature ranges of some water-soluble polymers can be found in U.S. Patent Application Publication Nos. 2009/0042766 and 2009/0082244. The disclosures of U.S. Patent Application Publication Nos. 2009/0042766 and 2009/0082244 are incorporated by reference in their entireties.

The water-soluble polymer can have, individually, a melting point temperature or a softening point temperature ranging, for example, from about 45° C. to about 275° C., about 75° C. to about 250° C., about 100° C. to about 225° C., about 125° C. to about 200° C., or about 150° C. to about 175° C.

The water-soluble polymer can have, individually, a melting point temperature or a softening point temperature ranging, for example, from about 45° C. to about 300° C., about 75° C. to about 300° C., about 100° C. to about 300° C., about 125° C. to about 300° C., about 150° C. to about 300° C., about 175° C. to about 300° C., about 200° C. to about 300° C., about 225° C. to about 300° C., about 250° C. to about 300° C., or about 275° C. to about 300° C.

The water-soluble polymer can have, individually, a melting point temperature or a softening point temperature ranging, for example, from about 45° C. to about 275° C., about 45° C. to about 250° C., about 45° C. to about 225° C., about 45° C. to about 200° C., about 45° C. to about 175°

C., about 45° C. to about 150° C., about 45° C. to about 125° C., about 45° C. to about 100° C., or about 45° C. to about 75° C.

The water-soluble polymer can have, individually, a melting point temperature or a softening point temperature ranging of, for example, about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., about 200° C., about 205° C., about 210° C., about 220° C., about 225° C., about 230° C., about 235° C., about 240° C., about 245° C., about 250° C., about 255° C., about 260° C., about 265° C., about 270° C., about 275° C., about 280° C., about 285° C., about 290° C., or about 295° C.

The water-soluble polymer can be, for example, a polyalkylene glycol, a polyethylene glycol, a polyethylene terephthalate, a polyvinyl alcohol, or any combination of these.

In one embodiment, the water soluble polymer can be a water-soluble colorant polymer.

In one embodiment, the composition can comprise the core or water soluble core comprising the carrier or water soluble carrier; a coating that at least partially covers the core or water-soluble core wherein the coating can comprise a water soluble-colorant polymer, and a colorant stabilizer; and a flow aid physically associated with the coating such that the flow aid is partially or fully exposed on an outer surface of the coating.

The amount of the water-soluble colorant polymer can be, for example, the same as the amount of the water-soluble polymer disclosed herein, the amount of the colorant disclosed herein, or can be a combination amount equivalent to a total amount of the water-soluble polymer and colorant disclosed herein.

The water-soluble colorant polymer can be, for example, acidic, basic, or neutral.

The water-soluble colorant polymer can, for example, have a net negative charge, a net positive charge, or a net neutral charge.

The water-soluble colorant polymer can, for example, have a weight average molecular weight that is the same as the polyethylene glycol (PEG) molecular weight discussed herein.

The water-soluble polymer can be contained in the STTC in an amount ranging, for example, from about 5% by weight to about 20% by weight, based on the weight of the STTC.

The water-soluble polymer can be contained in the STTC in an amount, for example, of about 6% by weight, about 7% by weight, about 8% by weight, about 9% by weight, about 10% by weight, about 11% by weight, about 12% by weight, about 13% by weight, about 14% by weight, about 15% by weight, about 16% by weight, about 17% by weight, about 18% by weight, or about 19% by weight, based on the weight of the STTC.

The water-soluble polymer can be, for example, a polyethylene glycol ("PEG"). The PEG can have a weight average molecular weight ranging, for example, from about 300 to about 10,000,000. Suitable PEGs can have a weight average molecular weight of, for example, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 11,000, about 15,000, about 20,000, about 25,000, about 30,000, about 35,000, about 40,000, about 45,000, about 50,000, about 55,000, about 60,000, about 65,000, about 70,000, about 75,000, about 80,000, about 85,000 about 90,000, about 95,000, about 100,000, about 200,000, about 300,000, about 400,000, about 500,000, about 600,000, about 700,000, about 800,000, about 900,000, about 1,000,000, about 2,000,000, about 3,000,000, about 4,000,000, about 5,000,000, about 6,000,000, about 7,000,000, about 8,000,000, about 9,000,000 or about 10,000,000.

The PEG can have a weight average molecular weight ranging, for example, from about 300 to about 10,000,000, from about 400 to about 10,000,00, from about 500 to about 10,000,000, from about 600 to about 10,000,000, from about 700 to about 10,000,000, from about 800 to about 10,000,000, from about 900 to about 10,000,000, from about 1,000 to about 10,000,000, from about 2,000 to about 10,000,000, from about 3,000 to about 10,000,000, from about 4,000 to about 10,000,000, from about 5,000 to about 10,000,000, from about 6,000 to about 10,000,000, from about 7,000 to about 10,000,000, from about 8,000 to about 10,000,000, from about 9,000 to about 10,000,000, from about 10,000 to about 10,000,000, from about from about 20,000 to about 10,000,000, from about 30,000 to about 10,000,000, from about 40,000 to about 10,000,000, from about 50,000 to about 10,000,000, from about 60,000 to about 10,000,000, from about 70,000 to about 10,000,000, from about 80,000 to about 10,000,000, from about 90,000 to about 10,000,000, from about 100,000 to about 10,000,000, from about 200,000 to about 10,000,000, from about 300,000 to about 10,000,000, from about 400,000 to about 10,000,000, from about 500,000 to about 10,000,000, from about 6000,000 to about 10,000,000, from about 700,000 to about 10,000,000, from about 800,000 to about 10,000,000, from about 900,000 to about 10,000,000, from about 1,000,000 to about 10,000,000, from about 2,000,000 to about 10,000,000, from about 3,000,000 to about 10,000,000, from about 4,000,000 to about 10,000,000, from about 5,000,000 to about 10,000,000, from about 6,000,000 to about 10,000,000, from about 7,000,000 to about 10,000,000, from about 8,000,000 to about 10,000,000, or from about 9,000,000 to about 10,000,000.

The PEG can have a weight average molecular weight, for example, ranging from about 300 to about 10,000,000, from about 300 to about 9,000,000, from about 300 to about 8,000,000, from about 300 to about 7,000,000, from about 300 to about 6,000,000, from about 300 to about 5,000,000, from about 300 to about 4,000,000, from about 300 to about 3,000,000, from about 300 to about 2,000,000, from about 300 to about 1,000,000, from about 300 to about 900,000, from about 300 to about 800,000, from about 300 to about 700,000, from about 300 to about 600,000, from about 300 to about 500,000, from about 300 to about 400,000, from about 300 to about 300,000, from about 300 to about 200,000, from about 300 to about 100,000, from about 300 to about 90,000, from about 300 to about 80,000, from about 300 to about 70,000, from about 300 to about 60,000, from about 300 to about 50,000, from about 300 to about 40,000, from about 300 to about 30,000, from about 300 to about 20,000, from about 300 to about 10,000, from about 300 to about 5,000, from about 300 to about 1,000, from about 300 to about 900, from about 300 to about 800, from about 300 to about 700, from about 300 to about 600, from about 300 to about 500, or from about 300 to about 400.

The PEG can have a weight average molecular weight ranging, for example, from about 3,000 to about 11,000, about 3,000 to about 10,000, about 3,000 to about 9,000, about 3,000 to about 8,000, about 3,000 to about 7,000, about 3,000 to about 6,000, about 3,000 to about 5,000, or about 3,000 to about 4,000.

The PEG can have a weight average molecular weight ranging, for example, from about 4,000 to about 12,000, about 5,000 to about 12,000, about 6,000 to about 12,000, about 7,000 to about 12,000, about 8,000 to about 12,000, about 9,000 to about 12,000, about 10,000 to about 12,000 or about 11,000 to about 12,000.

The PEG can have a weight average molecular weight ranging, for example, from about 7,000 to about 8,000, about 6,000 to about 9,000, about 5,000 to about 10,000, or about 4,000 to about 11,000.

Examples of PEGs are found in U.S. Pat. No. 7,871,976, which is incorporated by reference in its entirety.

The water-soluble polymer can be, for example, a polyethylene terephthalate.

The polyethylene terephthalate can be, for example, a polyester.

The water-soluble polymer, can be, for example, a polyvinyl alcohol. The polyvinyl alcohol can have, for example, a weight average molecular weight ranging from about 500 to about 100,000.

The weight average molecular weight of the polyvinyl alcohol can be, for example, about 600, about 700, about 800, about 900, about 1,000, about 5,000, about 10,000, about 15,000, about 20,000, about 25,000, about 30,000, about 35,000, about 40,000, about 45,000, about 50,000, about 55,000, about 60,000, about 65,000, about 70,000, about 75,000, about 80,000, about 85,000, about 90,000 or about 95,000.

The weight average molecular weight of the polyvinyl alcohol can range, for example, from about 1,000 to about 100,000, about 5,000 to about 100,000, about 10,000 to about 100,000, about 15,000 to about 100,000, about 20,000 to about 100,000, about 25,000 to about 100,000, about 30,000 to about 100,000, about 35,000 to about 100,000, about 40,000 to about 100,000, about 45,000 to about 100,000, about 50,000 to about 100,000, about 55,000 to about 100,000, about 60,000 to about 100,000, about 65,000 to about 100,000, about 70,000 to about 100,000, about 75,000 to about 100,000, about 80,000 to about 100,000, about 85,000 to about 100,000, about 90,000 to about 100,000, or about 95,000 to about 100,000.

The weight average molecular weight of the polyvinyl alcohol can range, for example, from about 1,000 to about 95,000, about 1,000 to about 90,000, about 1,000 to about 85,000, about 1,000 to about 80,000, about 1,000 to about 75,000, about 1,000 to about 70,000, about 1,000 to about 65,000, about 1,000 to about 60,000, about 1,000 to about 55,000, about 1,000 to about 50,000, about 1,000 to about 45,000, about 1,000 to about 40,000, about 1,000 to about 35,000, about 1,000 to about 30,000, about 1,000 to about 25,000, about 1,000 to about 20,000, about 1,000 to about 15,000, about 1,000 to about 10,000, or about 1,000 to 5,000.

In one embodiment, the weight average molecular weight of the polyvinyl alcohol can range, for example, from about 40,000 to about 60,000, about 35,000 to about 65,000, about 30,000 to about 70,000, about 25,000 to about 75,000, about 20,000 to about 80,000, about 15,000 to about 85,000, or about 10,000 to about 90,000.

The polyvinyl alcohol can have a degree of hydrolysis ranging, for example, from about 87 mol % to about 98 mol %.

The polyvinyl alcohol can have a degree of hydrolysis of, for example, about 87 mol %, about 88 mol %, about 89 mol %, about 90 mol %, about 91 mol %, about 92 mol %, about 93 mol %, about 94 mol %, about 95 mol %, about 96 mol %, or about 97 mol %.

The polyvinyl alcohol can have a degree of hydrolysis ranging, for example, from about 87 mol % to about 97 mol %, about 87 mol % to about 96 mol %, about 87 mol % to about 95 mol %, about 87 mol % to about 94 mol %, about 87 mol % to about 93 mol %, about 87 mol % to about 92 mol %, about 87 mol % to about 91 mol %, about 87 mol % to about 90 mol %, about 87 mol % to about 89 mol %, or about 87 mol % to about 88 mol %.

The polyvinyl alcohol can have a degree of hydrolysis ranging, for example, from about 88 mol % to about 98 mol %, about 89 mol % to about 98 mol %, about 90 mol % to about 98 mol %, about 91 mol % to about 98 mol %, about 92 mol % to about 98 mol %, about 93 mol % to about 98 mol %, about 94 mol % to about 98 mol %, about 95 mol % to about 98 mol %, about 96 mol % to about 98 mol %, or about 97 mol % to about 98 mol %.

The polyvinyl alcohol can have a degree of hydrolysis ranging, for example, from about 92 mol % to about 94 mol %, about 91 mol % to about 95 mol %, about 90 mol % to about 96 mol %, about 89 mol % to about 97 mol %, or about 88 mol % to about 98 mol %.

Perfumes

In one embodiment, the STTC does not comprise a perfume.

In another embodiment, the coating does not comprise a perfume.

In one embodiment, the STTC comprises a perfume.

In another embodiment, the perfume is present in the coating.

In a further embodiment, the perfume is present only in the coating.

Perfumes are discussed, for example, in U.S. Pat. No. 6,056,949. The contents of U.S. Pat. No. 6,056,949 are incorporated by reference in their entirety.

When present, the perfume can be contained for example, in an amount ranging from about 0.1% by weight to about 10% by weight, based on the weight of the STTC. The perfume can be contained, for example, in an amount of about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 2.0% by weight, about 3.0% by weight, about 4.0% by weight, about 5.0% by weight, about 6.0% by weight, about 7.0% by weight, about 8.0% by weight, or about 9.0% by weight, based on the weight of the STTC.

The perfume can be contained, for example, in an amount ranging from about 0.1% by weight to about 10% by weight, about 0.1% by weight to about 9% by weight, about 0.1% by weight to about 8% by weight, about 0.1% by weight to about 7% by weight, about 0.1% by weight to about 6% by weight, about 0.1% by weight to about 5% by weight, about 0.1% by weight to about 4% by weight, about 0.1% by weight to about 3% by weight, about 0.1% by weight to about 2% by weight, or about 0.1% by weight to about 1% by weight, based on the weight of the STTC.

The perfume can be contained, from example, in an amount ranging from about 1% by weight to about 10% by weight, about 2% by weight to about 10% by weight, about 3% by weight to about 10% by weight, about 4% by weight to about 10% by weight, about 5% by weight to about 10% by weight, about 6% by weight to about 10% by weight, about 7% by weight to about 10% by weight, about 8% by weight to about 10% by weight, or about 9% by weight to about 10% by weight, based on the weight of the STTC.

The perfume can be contained, for example, in an amount ranging from about 4% by weight to about 6% by weight, about 3% by weight to about 7% by weight, about 2% by weight to about 8% by weight, or about 1% by weight to about 9% by weight, based on the weight of the STTC.

The perfume can comprise an ester, an ether, an aldehyde, a ketone, an alcohol, a hydrocarbon, or any combination thereof.

The perfume can have, for example, a musky scent, a putrid scent, a pungent scent, a camphoraceous scent, an ethereal scent, a floral scent, a peppermint scent, or any combination thereof.

In one embodiment, the perfume can comprise methyl formate, methyl acetate, methyl butyrate, ethyl butyrate, isoamyl acetate, pentyl butyrate, pentyl pentanoate, octyl acetate, myrcene, geraniol, nerol, citral, citronellol, linalool, nerolidol, limonene, camphor, terpineol, alpha-ionone, thujone, benzaldehyde, eugenol, cinnamaldehyde, ethyl maltol, vanillin, anisole, anethole, estragole, thymol, indole, pyridine, furaneol, 1-hexanol, cis-3-hexenal, furfural, hexyl cinnamaldehyde, fructone, hexyl acetate, ethyl methyl phenyl glycidate, dihydrojasmone, oct-1-en-3-one, 2-acetyl-1-pyrroline, 6-acetyl -2,3,4,5-tetrahydropyridine, gamma-decalactone, gamma-nonalactone, delta-octalone, jasmine lactone, massoia lactone, wine lactone, sotolon, grapefruit mercaptan, methanthiol, methyl phosphine, dimethyl phosphine, nerolin, 2,4,6-trichloroanisole, or any combination thereof.

In one embodiment, the perfume can contain, for example, a linear terpene, a cyclic terpene, an aromatic compound, a lactone, a thiol, or any combination thereof.

In one embodiment, the perfume is High Five ACM 190991 F (Firmenich), Super Soft Pop 190870 (Firmenich), Mayflowers TD 485531 EB (Firmenich), or any combination thereof. Other art-known fragrances, or any fragrance commercially available from a fragrance supplier (e.g. Firmenich, Givaudan, etc.), or combinations of such fragrances, may also suitably be used in the STTCs, compositions, formulations, coatings, and methods disclosed herein.

At least some of the perfume can be encapsulated in a microcapsule.

In one embodiment, all of the perfume can be encapsulated in microcapsules.

The microcapsules can be water-soluble or water-insoluble.

Colorants

The coating can comprise a colorant and a colorant stabilizer. Applicants have unexpectedly found that the colorant can fade over time, changing hue or becoming essentially colorless or colorless. For example, Milliken Liquitint® colorants can fade when employed in a solid composition such as an STTC. Applicants have found that colorants, for example Milliken Liquitint® colorants, can be stabilized in a solid composition such as an STTC so that the colorants do not change hue or color or do not become substantially colorless or colorless. Stabilization is effected, in part or in whole, by a colorant stabilizer. Colorants, such as Milliken Liquitint® colorants, are thought to be stable over broad pH ranges and in diverse environments. Thus, it was surprising when test compositions such as STTCs containing colorants, for example Milliken Liquitint® colorants, became substantially colorless or colorless. It was equally surprising when adding an acid caused the color to return.

Without being bound by theory, it is possible that the colorant loses proton(s), which causes the colorant to change hue or become substantially colorless or colorless. The colorant stabilizer is believed to impart acidic proton(s) to the colorant, thereby stabilizing or restoring its color. Alternatively, the colorant stabilizer is believed to make the colorant more acidic, for example, by lowering the composition's pH.

The STTC or composition can have a pH ranging, for example, from about 2 to about 10. The pH of the STTC or composition can be, for example, about 2, about 3, about 4, about 5, about 6, about 7, about 8, about 9, or about 10.

The pH of the STTC or composition can range, for example, from about 2 to about 9, about 2 to about 8, about 2 to about 7, about 2 to about 6, about 2 to about 5, about 2 to about 4, or about 2 to about 3.

The pH of the STTC or composition can range, for example, from about 4 to about 8, about 4 to about 7, about 4 to about 6, or about 4 to about 5.

The pH of the STTC or composition can range, for example, from about 5 to about 8, about 6 to about 8, or about 7 to about 8.

The pH of the STTC or composition can range, for example, from about 2 to about 10, about 3 to about 10, about 4 to about 10, about 5 to about 10, about 6 to about 10, about 7 to about 10, about 8 to about 10, or about 9 to about 10.

The pH of the STTC or composition can be measured, for example, at room temperature by taking the pH of a 1% weight:volume solution of STTC or composition:water.

A solid composition such as an STTC, for example, in the absence of the colorant stabilizer, can become substantially colorless or colorless in a time period ranging from about 1 day to about 3 months.

For example, the solid composition or STTC, in the absence of the colorant stabilizer, can become substantially colorless or colorless in about 1 day, about 2 days, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, or about 11 weeks.

For example, the composition or STTC, in the absence of the colorant stabilizer, can become substantially colorless or colorless in at least 1 day, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks.

Colorants employed in the STTC can be, for example, Milliken Liquitint® colorants.

The colorants can be, for example, polymers.

The colorants can be, for example, dyes.

The colorants can be, for example, water-soluble polymeric colorants.

The colorants can be, for example, water-soluble dyes.

The colorants can be, for example, colorants that are well-known in the art or commercially available from dye or chemical manufacturers.

The color of the colorant is not limited, and can be, for example, red, orange, yellow, blue, indigo, violet, or any combination thereof.

The colorant can be, for example, one or more selected from the group consisting of Acid Blue 80, Acid Red 52, Acid Violet 48, and combinations thereof. When the colorant is one or more of these, the STTC, optionally, does not need to contain a colorant stabilizer. Surprisingly, it has been found that Acid Blue 80, Acid Red 52, and Acid Violet 48, do not display significant discoloration over time in solid compositions, STTCs, or liquid compositions, that do not contain a colorant stabilizer.

In one embodiment, the colorant can be present in the STTC's coating.

In one embodiment, the colorant is present only in the STTC's coating.

In one embodiment, the colorant can be present in an amount ranging from about 0.0001% by weight to about 0.1% by weight, based on the weight of the STTC.

The colorant can be present in, for example, in an amount of about 0.001% by weight, or about 0.01% by weight, based on the weight of the STTC.

The colorant can be present, for example, in an amount ranging from about 0.005% by weight to about 0.1% by weight, about 0.01% by weight to about 0.1% by weight, or about 0.05% by weight to about 0.1% by weight, based on the weight of the STTC.

Colorant Stabilizers

The colorant stabilizer can be, for example, an acid. The colorant stabilizer can be, for example, a Lewis acid or an Arrhenius acid or a Brønsted-Lowry acid.

In one embodiment, the colorant stabilizer bears an acidic proton.

In one embodiment, the colorant stabilizer has a positive molecular weight of about 1,000 daltons or less. The colorant stabilizer can have, for example, a positive molecular weight of about 900 daltons or less, about 800 daltons or less, about 700 daltons or less, about 600 daltons or less, about 500 daltons or less, about 400 daltons or less, about 300 daltons or less, about 200 daltons or less, or about 100 daltons or less.

The colorant stabilizer can have, for example, a molecular weight ranging from about 10 daltons to about 1,000 daltons.

The colorant stabilizer can have, for example, a molecular weight ranging from about 10 daltons to about 1,000 daltons, about 20 daltons to about 1,000 daltons, about 30 daltons to about 1,000 daltons, about 40 daltons to about 1,000 daltons, about 50 daltons to about 1,000 daltons, about 60 daltons to about 1,000 daltons, about 70 daltons to about 1,000 daltons, about 80 daltons to about 1,000 daltons, about 90 daltons to about 1,000 daltons, about 100 daltons to about 1,000 daltons, about 200 daltons to about 1,000 daltons, about 300 daltons to about 1,000 daltons, about 400 daltons to about 1,000 daltons, about 500 daltons to about 1,000 daltons, about 600 daltons to about 1,000 daltons, about 700 daltons to about 1,000 daltons, about 800 daltons to about 1,000 daltons, or about 900 daltons to about 1,000 daltons.

The colorant stabilizer can have, for example, a molecular weight range of from about 10 daltons to about 900 daltons, about 10 daltons to about 800 daltons, about 10 daltons to about 700 daltons, about 10 daltons to about 600 daltons, about 10 daltons to about 500 daltons, about 10 daltons to about 400 daltons, about 10 daltons to about 300 daltons, about 10 daltons to about 200 daltons, about 10 daltons to about 100 daltons, about 10 daltons to about 90 daltons, about 10 daltons to about 80 daltons, about 10 daltons to about 70 daltons, about 10 daltons to about 60 daltons, about 10 daltons to about 50 daltons, about 10 daltons to about 40 daltons, about 10 daltons to about 30 daltons, or about 10 daltons to about 20 daltons.

The colorant stabilizer can have, for example, a molecular weight ranging from about 400 daltons to about 600 daltons, about 300 daltons to about 700 daltons, about 200 daltons to about 800 daltons, or about 100 daltons to about 900 daltons.

The colorant stabilizer, in one embodiment, is not a polysaccharide.

In one embodiment, the colorant stabilizer is not a cellulose.

In one embodiment, the colorant stabilizer is not alginic acid.

In one embodiment, the colorant stabilizer is not algenic acid.

In one embodiment, the colorant stabilizer is not a polysaccharide, has a positive molecular weight of 1000 daltons or less, and bears an acidic proton.

In one embodiment, the colorant stabilizer is a small organic molecule.

In one embodiment, the colorant stabilizer is not a polysaccharide or a cellulose, and has a positive molecular weight of 1000 daltons or less, bears an acidic proton, and is a small organic molecule.

In one embodiment, the colorant stabilizer is a mineral acid.

In one embodiment, the colorant stabilizer is, for example, HF, HCl, HBr, HI, $H_2SO_4$, $HNO_3$, $H_3PO_4$, $H_3BO_3$, HClO, $HClO_2$, $HClO_3$, $HClO_4$, or any combination thereof.

In one embodiment, the colorant stabilizer is an organic molecule.

In one embodiment, the colorant stabilizer bears an acidic group which is an —OH group, a —C(O)OH group, a tetrazole, a hydroxamide, an acylcyanamide, a sulfonamide, a phosphonate, a sulfonate, a sulfonamide, a hydroxyisoxazole, an oxadiazolone, or any combination thereof.

In one embodiment, the colorant stabilizer is an alkyl carboxylic acid, a cycloalkyl carboxylic acid, heterocycloalkyl carboxylic acid, an amino acid, an aryl carboxylic acid, heteroaryl carboxylic acid, a cycloalkyl alkyl carboxylic acid, an aryl alkyl carboxylic acid, a heterocycloalkyl alkyl carboxylic acid, a heteroaryl alkyl carboxylic acid, an alcohol attached to an $sp^2$ hybridized carbon, any derivative thereof, or any combination thereof.

In one embodiment, the colorant stabilizer is formic acid, an acetic acid, a propanoic acid, a butanoic acid, a pentanoic acid, a hexanoic acid, a heptanoic acid, a octanoic acid, a nonanoic acid, a decanoic acid, a cyclopropyl carboxylic acid, a cyclobutyl carboxylic acid, a cyclopentyl carboxylic acid, a cyclohexyl carboxylic acid, a cycloheptyl carboxylic acid, a cyclooctyl carboxylic acid, a cyclononyl carboxylic acid, a cyclodecanoyl carboxylic acid, a lactic acid, a pyruvic acid, a phenol, an oxalic acid, a malonic acid, a succinic acid, a maleic acid, a fumaric acid, a glutaric acid, an adipic acid, a pimelic acid, a suberic acid, an azelaic acid, a sebacic acid, a citric acid, an ascorbic acid, an erythorbic acid, any derivative thereof, or any combination thereof.

In one embodiment, the colorant stabilizer comprises at least one —C(O)OH group, or at least one —C(O)OH groups, or at least three —C(O)OH groups, or at least four —C(O)OH groups.

In one embodiment, the colorant stabilizer is formic acid, citric acid, lactic acid, acetic acid, ascorbic acid, erythorbic acid, any derivative thereof, or any combination thereof.

In one embodiment, the colorant stabilizer is citric acid.

In one embodiment, the colorant stabilizer is contained only in the coating.

In one embodiment, the colorant stabilizer is a fatty acid.

In one embodiment, the colorant stabilizer is a saturated fatty acid.

In one embodiment, the colorant stabilizer is an unsaturated fatty acid that is a mono-unsaturated or poly-unsaturated fatty acid.

In one embodiment, the colorant stabilizer is a nucleic acid.

The colorant stabilizer can be present in the STTC, the composition, or the coating, individually, for example, in an amount ranging from about 0.1% by weight to about 2.0% by weight, based on the weight of the STTC, the composition, or the coating.

The colorant stabilizer can be present, individually, for example, in an amount of about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.1% by weight, about 1.2% by weight, about 1.3% by weight, about 1.4% by weight, about 1.5% by weight, about 1.6% by weight, about 1.7% by weight, about 1.8% by weight, about 1.9% by weight, or about 2.0% by weight, based on the weight of the STTC, the composition, or the coating.

The colorant stabilizer can be present in the STTC, the composition, or the coating, individually, for example, in an amount ranging from about 0.1% by weight to about 1.9% by weight, about 0.1% by weight to about 1.8% by weight, about 0.1% by weight to about 1.7% by weight, about 0.1% by weight to about 1.6% by weight, about 0.1% by weight to about 1.5% by weight, about 0.1% by weight to about 1.4% by weight, about 0.1% by weight to about 1.3% by weight, about 0.1% by weight to about 1.2% by weight, about 0.1% by weight to about 1.1% by weight, about 0.1% by weight to about 1.0% by weight, about 0.1% by weight to about 0.9% by weight, about 0.1% by weight to about 0.8% by weight, about 0.1% by weight to about 0.7% by weight, about 0.1% by weight to about 0.6% by weight, about 0.1% by weight to about 0.5% by weight, about 0.1% by weight to about 0.4% by weight, about 0.1% by weight to about 0.3% by weight, or about a 0.1% by weight to about 0.2% by weight, based on the weight of the STTC, the composition, or the coating.

The colorant stabilizer, in one embodiment, can be present, individually, in the STTC, the composition, or the coating, in an amount sufficient to bring a 0.1% water solution of weight:volume STTC or composition to water, to a pH of from about 2.0 to about 8.0.

The colorant stabilizer, in one embodiment, can be present individually, in the STTC, the composition, or the coating, in an amount sufficient to bring a 0.1% water solution of weight:volume STTC or composition to water, to a pH of about 2.0, about 3.0, about 4.0, about 5.0, about 6.0, about 7.0, or about 8.0.

In one embodiment, the colorant-stabilizer is contained in the composition or STTC or coating along with a polysaccharide, which can be a cellulose, or a derivative thereof.

In one embodiment, the colorant-stabilizer and a polysaccharide, which can be a cellulose, or a derivative thereof, are contained in the coating of a composition or STTC.

In one embodiment, the composition or STTC contains a colorant-stabilizer and a polysaccharide, which can be a cellulose, or a derivative thereof, in amounts such that the colorant-stabilizer and the polysaccharide, which can be a cellulose, or a derivative thereof, synergistically stabilize the colorant.

If present, the polysaccharide, which can be a cellulose, or a derivative thereof, can be present in the composition or the STTC or the coating, individually, for example, an in an amount ranging from 0.1% to 10% by weight, based on the weight of the STTC, the composition, or the coating. The polysaccharide, which can be a cellulose, or a derivative thereof, can be present, for example, in an amount of about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 2.0% by weight, about 3.0% by weight, about 4.0% by weight, about 5.0% by weight, about 6.0% by weight, about 7.0% by weight, about 8.0% by weight, about 9.0% by weight, or about 10% by weight, based on the weight of the STTC, the composition, or the coating.

Flow Aids

In one embodiment, the flow aid comprises a fabric softener.

In a further embodiment, the flow aid is partially exposed on an outer surface of the coating.

In an additional embodiment, the flow aid is mixed into the coating.

In another embodiment, the flow aid is homogeneously mixed into the coating.

In an additional embodiment, the fabric softener is a polysiloxane, a textile-softening clay, a cationic polymer, or any combination thereof.

In one embodiment, the STTC does not does not contain a clay and a cationic polymer at the same time.

In one embodiment, the STTC contains a clay and a cationic polymer at the same time.

In a further embodiment, the fabric softener is a polysiloxane.

In one embodiment, the fabric softener is a textile-softening clay.

In another embodiment, the fabric softener is a textile-softening clay which is a smectite clay.

In a further embodiment, the smectite clay is a Bentonite clay, Beidellite clay, a Hectorite clay, a Laponite clay, a Montmorillonite clay, a Nontronite clay, a Saponite clay, a Sauconite, clay, or any combination thereof.

In one embodiment, the smectite clay is a Laponite clay.

In another embodiment, the smectite clay is a Bentonite clay.

In one embodiment, the flow aid does not comprise a fabric softener.

In an embodiment, the flow aid comprises an inorganic alkali metal salt, an inorganic alkaline earth metal salt, a silicate, an aluminosilicate, an amorphous silica, or any combination thereof.

In one embodiment, flow aid comprises sodium sulfate.

In another embodiment, the flow aid is or comprises Zeofree 5161 (J.M. Huber Corpn.; Edison, N.J.).

In one embodiment, a cationic polymer defined to include polymers which, because of their molecular weight or monomer composition, are soluble or dispersible to at least the extent of 0.01% by weight in distilled water at 25° C. Water soluble cationic polymers can include polymers in which one or more of the constituent monomers are selected from the list of copolymerizable cationic or amphoteric monomers. These monomer units contain a positive charge over at least a portion of the pH range 6-11. A partial listing of monomers can be found in the "International Cosmetic Ingredient Dictionary," 5th Edition, edited by J. A. Wenninger and G. N. McEwen, The Cosmetic, Toiletry, and Fragrance Association, 1993. Another source of such monomers can be found in "Encyclopedia of Polymers and Thickeners for Cosmetics", by R. Y. Lochhead and W. R. Fron, Cosmetics & Toiletries, vol. 108, May 1993, pp 95-135.

The cationic polymers of the present invention can be amine salts or quaternary ammonium salts. Preferably the cationic polymers are quarternary ammonium salts. They includes cationic derivatives of natural polymers such as polysaccharide, polyquaternium 10, UCARE Polymer JR-400, UCARE Polymer LR-400, starch and their copolymers with certain cationic synthetic polymers such as polymers and co-polymers of cationic vinylpyridine or vinyl pyridinium chloride.

Specifically, monomers useful in this invention may be represented structurally as etiologically unsaturated compounds as in formula I:

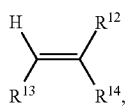

wherein $R^{12}$ is hydrogen, hydroxyl, methoxy, or a $C_1$ to $C_{30}$ straight or branched alkyl radical; $R^{13}$ is hydrogen, or a $C_{1\text{-}30}$ straight or branched alkyl, a $C_{1\text{-}30}$ straight or branched alkyl substituted aryl, aryl substituted $C_{1\text{-}30}$ straight or branched alkyl radical, or a poly oxyalkene condensate of an aliphatic radical; and $R^{14}$ is a heteroatomic alkyl or aromatic radical containing either one or more quaternized nitrogen atoms or one or more amine groups which possess a positive charge over a portion of the pH interval pH 6 to 11. Such amine groups can be further delineated as having a $pK_a$ of about 6 or greater.

Examples of cationic monomers of formula I include, but are not limited to, co-poly 2-vinyl pyridine and its co-poly 2-vinyl N-alkyl quaternary pyridinium salt derivatives; co-poly 4-vinyl pyridine and its co-poly 4-vinyl N-alkyl quaternary pyridinium salt derivatives; co-poly 4-vinylbenzyltrialkylammonium salts such as co-poly 4-vinylbenzyltrimethylammonium salt; co-poly 2-vinyl piperidine and co-poly 2-vinyl piperidinium salt; co-poly 4-vinylpiperidine and co-poly 4-vinyl piperidinium salt; co-poly 3-alkyl 1-vinyl imidazolium salts such as co-poly 3-methyl 1-vinyl imidazolium salt; acrylamide and methacrylamido derivatives such as co-poly dimethyl aminopropylmethacrylamide, co-poly acrylamidopropyl trimethylammonium salt and co-poly methacrylamidopropyl trimethylammonium salt; acrylate and methacrylate derivatives such as co-poly dimethyl aminoethyl(meth)acrylate, co-poly ethanaminium N,N,N trimethyl 2-[(1-oxo-2 propenyl)oxy]-salt, co-poly ethanaminium N,N,N trimethyl 2-[(2 methyl-1-oxo-2 propenyl)oxy]-salt, and co-poly ethanaminium N,N,N ethyl dimethyl 2-[(2 methyl-1-oxo-2 propenyl)oxy]-salt.

Also included among the cationic monomers suitable for this invention are co-poly vinyl amine and co-polyvinylammonium salt; co-poly diallylamine, co-poly methyldiallylamine, and co-poly diallydimethylammonium salt; and the ionene class of internal cationic monomers. This class includes co-poly ethylene imine, co-poly ethoxylated ethylene imine and co-poly quaternized ethoxylated ethylene imine; co-poly [(dimethylimino)trimethylene(dimethylimino)hexamethylene disalt], co-poly [(diethylimino)trimethylene(dimethylimino)trimethylene disalt]; co-poly [(dimethylimino)-2-hydroxypropyl salt]; co-polyquartemium-2, co-polyquartemium-17, and co-polyquartemium 18, as defined in the "International Cosmetic Ingredient Dictionary" edited by Wenninger and McEwen.

An additional, and highly preferred class of cationic monomers suitable for this invention are those arising from natural sources and include, but are not limited to, cocodimethylammonium hydroxypropyl oxyethyl cellulose, lauryldimethylammonium hydroxypropyl oxyethyl cellulose, stearyldimethylammonium hydroxypropyl oxyethyl cellulose, and stearyldimethylammonium hydroxyethyl cellulose; guar 2-hydroxy-3-(trimethylammonium) propyl ether salt; and cellulose 2-hydroxyethyl 2-hydroxy 3-(trimethyl ammonio)propyl ether salt.

The counterion of the comprising cationic co-monomer is freely chosen from the halides: chloride, bromide, and iodide; or from hydroxide, phosphate, sulfate, hydrosulfate, ethyl sulfate, methyl sulfate, formate, and acetate.

The weight fraction of the cationic polymer which is composed of the above-described cationic monomer units can range from 1 to 100%, preferably from 10 to 100%, and most preferably from 15 to 80% of the entire polymer. The remaining monomer units comprising the cationic polymer are chosen from the class of anionic monomers and the class of nonionic monomers or solely from the class of nonionic monomers. In the former case, the polymer is an amphoteric polymer while in the latter case it can be a cationic polymer, provided that no amphoteric co-monomers are present. Amphoteric polymers should also be considered within the scope of thris disclosure, provided that the polymer unit possesses a net positive charge at one or more points over the wash pH range of pH 6 to 11.

The class of nonionic monomers include, but are not limited to, vinyl alcohol; vinyl acetate; vinyl methyl ether; vinyl ethyl ether; acrylamide, methacrylamide and other modified acrylamides; vinyl propionate; alkyl acrylates (esters of acrylic or methacrylic acid); and hydroxyalkyl acrylate esters. A second class of nonionic monomers include co-poly ethylene oxide, co-poly propylene oxide, and co-poly oxymethylene. A third, and highly preferred, class of nonionic monomers includes naturally derived materials such as hydroxyethylcellulose.

Many of the aforementioned cationic polymers can be synthesized in, and are commercially available in, a number of different molecular weights. In order to achieve optimal cleaning and softening performance from the product, it is desirable that the water-soluble cationic or amphoteric polymer used in this invention be of an appropriate molecular weight. Without wishing to be bound by theory, it is believed that polymers that are too high in mass can entrap soils and prevent them from being removed. The use of cationic polymers with an average molecular weight of less than about 850,000 daltons, and especially those with an average molecular weight of less than 500,000 daltons can help to minimize this effect without significantly reducing the softening performance of properly formulated products. On the other hand, polymers with a molecular weight of about 10,000 daltons or less are believed to be too small to give an effective softening benefit.

In addition, the charge density of the cationic polymer can affect either softening or staining removal. The charge density relates to the degree of cationic substitution, and can be expressed with Nitrogen content of a cationic polymer. Preferred are cationic polymer having a N % from 0.01 to 2.2%, and more preferred are cationic polymers having a N % from 0.2 to 1.6%, and most preferred are cationic polymers having a N % from 0.3 to 1.4%.

Additional Ingredients

In another embodiment, the STTC further comprises an additive known to be employed in textile-treating compositions.

The additive can be comprised in the core, in the water-soluble core, in the coating, can be physically associated with the coating such that the additive is partially or fully exposed on an outer or inner surface of the coating, in the flow aid, or any combination thereof.

The additive can be, for example, a bleaching agent, a bleach activator, an enzyme, a silicone oil, an anti-redeposition agent, an optical brightener, a greying inhibitor, a shrink inhibitor, an anti-creasing agent, a color transfer inhibitor, an anti-microbial, a germicide, a fungicide, an anti-oxidant, an anti-static agent, an ironing aid, a water proofing agent, an impregnation agent, a swelling agent, an anti-slip agent, a UV absorber, a corrosion inhibitor, or any combination thereof. In other embodiments, the additive can be one or more viscosity-modifying agents (e.g., silica, sodium CMC, and other agents well-known in the art to increase or decrease the viscosity of a liquid or liquid-containing suspension), one or more opacifying agents, and the like.

The additive can be, for example, contained in the STTC in an amount ranging from about 0.00001% by weight to about 10% by weight, based on the weight of the STTC.

The additive can comprise, for example, about 0.0001% by weight, about 0.001% by weight, about 0.01% by weight, about 0.1% by weight, about 1% by weight, about 2% by weight, about 3% by weight, about 4% by weight, about 5% by weight, about 6% by weight, about 7% by weight, about 8% by weight or about 9% by weight, based on the weight of the STTC.

For example, the amount of additive in the STTC can range, for example, from about 0.0001% by weight to about 9% by weight, about 0.0001% by weight to about 8% by weight, about 0.0001% by weight to about 7% by weight, about 0.0001% by weight to about 6% by weight, about 0.0001% by weight to about 5% by weight, about 0.0001% by weight to about 4% by weight, about 0.0001% by weight to about 3% by weight, about 0.0001% by weight to about 2% by weight, or about 0.0001% by weight to about 1% by weight, based on the weight of the STTC.

The additive can be contained in the STTC, for example, in an amount ranging from about 0.00001% by weight to about 10% by weight, about 0.0001% by weight to about 10% by weight, about 0.001% by weight to about 10% by weight, about 0.01% by weight to about 10% by weight, about 0.1% by weight to about 10% by weight, about 1% by weight to about 10% by weight, about 2% by weight to about 10% by weight, about 3% by weight to about 10% by weight, about 4% by weight to about 10% by weight, about 5% by weight to about 10% by weight, about 6% by weight to about 10% by weight, about 7% by weight to about 10% by weight, about 8% by weight to about 10% by weight, or about 9% by weight to about 10% by weight, based on the weight of the STTC.

Cleaning Agent Compositions

One inventive embodiment is a cleaning agent composition comprising a detergent and an STTC. The detergent can comprise a surfactant. The surfactant can be, for example, a neutral surfactant, a cationic surfactant, an anionic surfactant, a zwitterionic surfactant, or any combination thereof.

Contained Compositions

One inventive embodiment is a container containing an STTC or a cleaning agent composition. The container can comprise, for example, plastic, paper, metal, or any combination thereof. The container can contain instructions for using the STTC or cleaning agent composition contained therein. The instructions can be in any language, for example, in English, Spanish, German, French, or Dutch.

In certain such embodiments, the container is a water-soluble container, such as a pouch. Unit dose containers and methods of manufacture thereof that are suitable for use with the STTCs or cleaning agent compositions of the present invention include those described, for example, in U.S. Pat. Nos. 3,218,776; 4,776,455; 6,727,215; 6,878,679; 7,259,134; 7,282,472; 7,304,025; 7,329,441; 7,439,215; 7,464,519; and 7,595,290; and in U.S. Published Application No. 2012/0108487 A1; the disclosures of all of which are incorporated herein by reference in their entireties. In preferred such embodiments, the container is a water-soluble, single-chamber container, prepared from a water-soluble film. According to one such aspect of the invention, the single-chamber container is a formed, sealed pouch produced from a water-soluble polymer or film such as polyvinylalcohol (PVOH) or a PVOH film.

The water soluble container used in the compositions of the present invention is made from a water-soluble material which dissolves, ruptures, disperses, or disintegrates upon contact with water, releasing thereby the composition or cleaning system contained within the container. In preferred, the single-chamber or -compartment sealed water soluble container, which may be in the form of a pouch, is formed from a water soluble polymer. Non-limiting examples of suitable such water soluble polymers include polyvinyl alcohol, cellulose ethers, polyethylene oxide, starch, polyvinylpyrrolidone, polyacrylamide, polyacrylonitrile, polyvinyl methyl ether-maleic anhydride, polymaleic anhydride, styrene maleic anhydride, hydroxyethylcellulose, methylcellulose, polyethylene glycols, carboxymethylcellulose, polyacrylic acid salts, alginates, acrylamide copolymers, guar gum, casein, ethylene-maleic anhydride resins, polyethyleneimine, ethyl hydroxyethylcellulose, ethyl methylcellulose, hydroxyethyl methylcellulose, and mixtures thereof. In one embodiment, the water soluble container is made from a lower molecular weight water-soluble polyvinyl alcohol film-forming resin.

Preferred water soluble polymers for forming the pouch are polyvinyl alcohol (PVOH) resins sold under tradename MONOSOL® (MonoSol LLC, Indiana). The preferred grade is MONOSOL® film having a weight average molecular weight range of about 55,000 to 65,000 and a number average molecular weight range of about 27,000 to 33,000. Preferably, the film material will have a thickness of approximately 3 mil or 75 micrometers. Alternatively, commercial grade PVOH films are suitable for use in the present invention, such as those that are commercially available from Monosol (Merrillville, Ind.) (e.g., Monosol film M8630) or from Aicello (Aiichi, Japan; North American subsidiary in North Vancouver, BC, Canada) (e.g., Aicello fil PT75).

In some embodiments, the water soluble container further comprises a cross-linking agent. In some embodiments, the cross-linking agent is selected from the group consisting of formaldehyde, polyesters, epoxides, isocyanates, vinyl esters, urethanes, polyimides, acrylics with hydroxyl, carboxylic, isocyanate or activated ester groups, bis(methacryloxypropyl)tetramethylsiloxane (styrenes, methylmetacrylates), n-diazopyruvates, phenylboronic acids, cis-platin, divinylbenzene (styrenes, double bonds), polyamides, dialdehydes, triallyl cyanurates, N-(2-ethanesulfonylethyl)pyridinium halides, tetraalkyltitanates, titanates, borates, zirconates, or mixtures thereof. In one embodiment, the cross-linking agent is boric acid or sodium borate, In additional embodiments, the water-soluble container or film from which it is made can contain one or more additional components, agents or features, such as one or more perfumes or fragrances, one or more enzymes, one or more surfactants, one or more rinse agents, one or more dyes, one or more functional or aesthetic particles, and the like. Such components, agents or features can be incorporate into or on the film when it is manufactured, or are conveniently introduced onto the film during the process of manufacturing the cleaning compositions of the present invention, using methods that are known in the film-producing arts.

In some embodiments, the water soluble container comprises a protective layer between the film polymer and the composition in the pouch. In some embodiments, the protective layer comprises polytetrafluoroethylene (PTFE).

The single-compartment, water-soluble container (e.g., pouch) used in association with the present compositions may be in any desirable shape and size and may be prepared in any suitable way, such as via molding, casting, extruding or blowing, and is then filled using an automated filling process. Examples of processes for producing and filling water-soluble containers, suitable for use in accordance with the present invention, are described in U.S. Pat. Nos. 3,218,776; 3,453,779; 4,776,455; 5,699,653; 5,722,217; 6,037,319; 6,727,215; 6,878,679; 7,259,134; 7,282,472; 7,304,025; 7,329,441; 7,439,215; 7,464,519; and 7,595,290; the disclosures of all of which are incorporated herein by reference in their entireties. In preferred embodiments, the pouches are filled with the STTC and/or the cleaning agent composition of the present invention using the cavity filling approach described in U.S. Pat. Nos. 3,218,776 and 4,776,455; machinery necessary for carrying out this process is commercially available, e.g., from Cloud Packaging Solutions (Des Plaines, Ill.; a division of Ryt-way Industries, LLC, Lakeville, Minn.).

Methods

In one embodiment is provided a method for making an STTC. The method comprises at least partially or fully coating a core with a coating, and applying a flow aid to the partially or fully coated core to form the STTC. The core can comprise a carrier, the carrier can be water-soluble, the core can be water-soluble, and the core or water-soluble core can consist of the carrier or water-soluble carrier. The coating can comprise, for example, a colorant, a water-soluble polymer, and a colorant stabilizer. The coating can further comprise a perfume. The flow aid can comprise a fabric softener. The flow aid can be physically associated with the coating such that the flow aid is partially or fully exposed on an outer surface of the coating.

In another embodiment is provided a method for making a cleaning agent composition comprising blending or mixing or combining an STTC and a detergent. The detergent can comprise a surfactant.

The ratio of detergent to STTC can be, for example, about 100:1 to about 1:100, on a weight to weight basis.

The ratio of detergent to STTC can be, for example, about 90:1, about 80:1, about 70:1, about 60:1, about 50:1, about 40:1, about 30:1, about 20:1, about 10:1, about 1:10, about 1:20, about 1:30, about 1:40, about 1:50, about 1:60, about 1:70, about 1:80, or about 1:90, on a weight to weight basis.

In another embodiment, is provided a method of treating a textile comprising combining or mixing or blending the textile, water, and an STTC. The amount of STTC can be, for example, about 0.001 g to about 1 kg. The amount of the STTC can be, for example, about 0.01 g, about 0.1 g, about 1 g, about 2 g, about 3 g, about 4 g, about 5 g, about 6 g, about 7 g, about 8 g, about 9 g, about 10 g, about 25 g, about 50 g, about 100 g, about 200 g, about 300 g, about 400 g, about 500 g, about 600 g, about 700 g, about 800 g, or about 900 g.

In a further embodiment, is provided a method of cleaning or cleaning and treating a textile with a cleaning agent composition comprising combining or mixing or blending the textile, water, and a cleaning agent composition. The amount of the cleaning agent composition can be, for example, about 0.001 g to about 1 kg. The amount of cleaning agent composition can be, for example, about 0.01 g, about 0.1 g, about 1 g, about 2 g, about 3 g, about 4 g, about 5 g, about 6 g, about 7 g, about 8 g, about 9 g, about 10 g, about 25 g, about 50 g, about 100 g, about 200 g, about 300 g, about 400 g, about 500 g, about 600 g, about 700 g, about 800 g, or about 900 g.

In another embodiment is provided a method of stabilizing a colorant in a granular composition, a solid composition, or a liquid composition, comprising stabilizing the colorant with a colorant stabilizer. The colorant stabilizer can be incorporated into the composition. In one embodiment, where the composition is structured, the colorant stabilizer is incorporated into the same substructure as the colorant or in a different substructure, or in one, or two, or three, or more, or all substructures.

In a further embodiment is provided a method of visually designating when a granular composition, a solid composition, or a liquid composition, has passed its pull date by the composition becoming substantially colorless or colorless, comprising blending or combining or mixing the colorant stabilizer in the composition with the colorant in an amount such that the composition does not become substantially colorless or colorless until at or about at its pull date. Thus, in one embodiment, an STTC or composition can be formulated with a colorant and a colorant stabilizer such that the STTC or the composition does not become substantially colorless or colorless until at or about at its pull date.

Compositions Made by Methods

In one embodiment is provided an STTC made by a method. The method comprises at least partially or fully coating a core with a coating, and applying a flow aid to the partially or fully coated core to form the STTC. The core can comprise a carrier, the carrier can be water-soluble, the core can be water-soluble, and the core or water-soluble core can consist of the carrier or water-soluble carrier. The coating can comprise, for example, a colorant, a water-soluble polymer, and a colorant stabilizer. The coating can further comprise a perfume. The flow aid can comprise a fabric softener. The flow aid can be, for example, physically associated with the coating such that the flow aid is partially or fully exposed on an outer surface of the coating.

In another embodiment is provided cleaning agent composition made by a method comprising blending or mixing or combining an STTC and a detergent. The detergent can comprise a surfactant.

A ratio of detergent to STTC can be, for example, about 100:1 to about 1:100, on a weight to weight basis. The ratio of detergent to STTC can be, for example, about 90:1, about 80:1, about 70:1, about 60:1, about 50:1, about 40:1, about 30:1, about 20:1, about 10:1, about 1:10, about 1:20, about 1:30, about 1:40, about 1:50, about 1:60, about 1:70, about 1:80, or about 1:90, on a weight to weight basis.

In another embodiment is a granular composition or solid composition made by a process comprising mixing or blending or combining a colorant and a colorant stabilizer to form the solid composition. The solid or granular composition can be structured. The solid or granular composition can be an STTC. When the solid or granular composition is structured, the colorant and the colorant stabilizer can be in same substructure or layer or in a different substructure or layer or in one or two or three or all substructures. In the composition, the colorant is stabilized at least in part by the colorant stabilizer.

The colorant can be stabilized for various period of time, for example for about 1 week to about 10 years.

The colorant can be stabilized, for example, for about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years, about 7 years, about 8 years, or about 9 years.

The colorant can be stabilized, for example, for at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 3 years, at least 4 years, at least 5 years, at least 6 years, at least 7 years, at least 8 years, at least 9 years, or at least 10 years.

Solid Wash Cycle Conditioning Agents ("SWCCAs")

In another embodiment is provided SWCCAs.

U.S. Pat. No. 7,871,976 discloses laundry scent additives having polyethylene glycol and perfume that, in some embodiments, can be in the form of a pastille.

Applicants have found, unexpectedly, that SWCCAs described herein are desirably both solid at about 25° C. and soluble in cold, warm, and hot water, while delivering one or more of good detergency, long lasting fragrance impression, textile softening, or decreased textile static build up when an SWCCA treated textile is subsequently dried in a dryer or dried while a textile is hanging on a line.

The SWCCA can comprise, for example, one or more non-ionic surfactants, one or more fabric conditioning agents, optionally one or more plasticizers, optionally one or more colorants, optionally one or more colorant stabilizers, and optionally one or more perfames. In some embodiments, the SWCCA can fully or partially coat a core.

The ingredients in the SWCCA can be homogeneously or heterogeneously mixed.

In some embodiments, the ingredients in the SWCCA are homogeneously mixed.

Non-Ionic Surfactant(s)

The non-ionic surfactant(s) can be, for example, hydroxyl -hydroxypoly(oxyethylene)poly(oxypropylene)-poly(oxyethylene)-block copolymer(s) (e.g., hydroxyl terminated EO/PO/EO block copolymer(s)). The block copolymer(s) can be, for example ethyleneoxide/propylene oxide block copolymer(s) (EP/PO copolymers). The block copolymer(s) can be, for example, PO/EO/PO block copolymer(s), EO/PO block copolymer(s), or PO/EO block copolymer(s), all of which may optionally be hydroxyl terminated at one or both ends.

The non-ionic surfactant or block copolymer(s) can have, individually, hydrophilic-lipophilic-balance (HLB).

The HLB can be calculated, for example, using the methodology of Griffin or Davies (Griffin, W. C., "Classification of Surface-Active Agents by 'HLB'," *J Soc. Cosmetic Chemists* 1:311 (1949); Davies, J. T., "A Quantitative Kinetic Theory of Emulsion Type, I. Physical Chemistry of the Emulsifying Agent," Gas/Liquid and Liquid/Liquid Interface. *Proceedings the International Congress of Surface Activity* 426-438 (1957). Davies' methodology is useful for calculating higher HLB values. McCutcheon's Emulsifiers and Detergents, alternatively, provides HLB values for commercially available nonionic surfactants.

The non-ionic surfactant(s) or block copolymer(s) can have, for example, individually, an HLB ranging from about 19 to about 35.

The non-ionic surfactant(s) or block copolymer(s) can have, for example, individually, an HLB ranging from about 20 to about 35, from about 22 to about 35, from about 24 to about 35, from about 25 to about 35, from about 26 to about 35, from about 28 to about 35, from about 30 to about 35, from about 32 to about 35, from about 32 to about 19, from about 30 to about 19, from about 28 to about 19, from about 25 to about 19, from about 24 to about 19, from about 22 to about 19, from about 20 to about 19, from about 22 to about 33, from about 24 to about 31, or from about 25 to about 29.

The non-ionic surfactant(s) or block copolymer(s) can have, for example, individually, an HLB of at least 20, at least 22, at least 24, at least 25, at least 26, at least 28, at least 30, at least 32, or at least 35.

The non-ionic surfactant(s) or block copolymer(s) can have, for example, individually, an HLB of about 20, about 22, about 24, about 25, about 26, about 28, about 30, about 32, or about 34.

The non-ionic surfactant(s) or block copolymer(s) can have, individually, a weight average molecular weight ranging, for example, from about 3,000 to about 12,000. The weight average molecular weight can range, for example, from about 3,500 to about 12,000, from about 4,000 to about 12,000, from about 4,500 to about 12,000, from about 5,000 to about 12,000, from about 5,500 to about 12,000, from about 6,000 to about 12,000, from about 6,500 to about 12,000, from about 7,000 to about 12,000, from about 7,500 to about 12,000, from about 8,000 to about 12,000, from about 8,500 to about 12,000, from about 9,000 to about 12,000, from about 9,500 to about 12,000, from about 10,000 to about 12,000, from about 10,500 to about 12,000, from about 11,000 to about 12,000, from about 11,500 to about 12,000, from about 11,500 to about 3,000, from about 11,000 to about 3,000, from about 10,500 to about 3,000, from about 10,000 to about 3,000, from about 9,500 to about 3,000, from about 9,000 to about 3,000, from about 8,500 to about 3,000, from about 8,000 to about 3,000, from about 7,500 to about 3,000, from about 7,000 to about 3,000, from about 6,500 to about 3,000, from about 6,000 to about 3,000, from about 5,500 to about 3,000, from about 5,000 to about 3,000, from about 4,500 to about 3,000, from about 4,000 to about 3,000, from about 3,500 to about 3,000, from about 3,200 to about 11,400, from about 3,500 to about 11,000, from about 4,000 to about 10,500, from about 4,500 to about 10,000, from about 4,700 to about 8,400, or from about 5,500 to about 7,000.

Examples of non-ionic surfactant(s) or block copolymer(s) include, but are not limited to, PLURONIC-F38 (BASF), PLURONIC-F68 (BASF), PLURONIC-F77 (BASF), PLURONIC-F87 (BASF) and PLURONIC-F88 (BASF).

The SWCCA can contain a total amount of the non-ionic surfactant(s) or block copolymer(s), for example, in an amount ranging from about 90% by weight to about 60% by weight, based on the weight of the SWCCA.

The non-ionic surfactant(s) or block co-polymer(s) can be, for example, contained in the SWCCA in a total amount ranging from about 90% by weight to about 65% by weight, from about 90% by weight to about 70% by weight, from about 90% to about 75% by weight, from about 90% to about 80% by weight, from about 90% by weight to about 85% by weight, from about 60% by weight to about 85% by weight, from about 60% by weight to about 80% by weight, from about 60% by weight to about 75% by weight, from about 60% by weight to about 70% by weight, from about 60% by weight to about 65% by weight, from about 70% by weight to about 80% by weight, based on the weight of the SWCCA.

In some embodiments, for example, some or all of the total amount of non-ionic surfactant(s) or block copolymer(s) in the SWCCA can be replaced by or be one or more sorbitan esters. The sorbitan esters can be, for example, optionally ethoxylated and/or propyloxylated and/or esterified with a fatty acid. When optionally esterified with a fatty acid, the sorbitan esters can form, for example, one or more of a monolaurate, a monopalmitate, a monostearate, or a monooleate. The one or more sorbitan esters can be one or more polysorbates. Examples of polysorbates, include, but are not limited to, one or more of the following polysorbates: 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 and 85.

In some embodiments, the polysorbate can be one or more of the following polysorbates: 20, 21, 40, 60, 61, 65, 80 and 85. In some embodiments, the, sorbitan ester is Tween 61.

The one or more sorbitan esters or polysorbates when present, can be or replace, for example, from about 1% to about 100% of the total amount of the non-ionic surfactant(s) or block copolymer(s) in the SWCCA.

The sorbitan esters or polysorbates can be or replace replace, for example, from about 10% to about 100%, from about 20% to about 100%, from about 30% to about 100%, from about 40% to about 100%, from about 50% to about 100%, from about 60% to about 100%, from about 70% to about 100%, from about 80% to about 100%, from about 90% to about 100%, from about 1% to about 90%, from about 1% to about 80%, from about 1% to about 70%, from about 1% to about 60%, from about 1% to about 50%, from about 1% to about 40%, from about 1% to about 30%, from about 1% to about 20%, from about 1% to about 10%, from about 10% to about 90%, from about 20% to about 80%, from about 30% to about 70%, or from about 40% to about 60%, of the total weight of the non-ionic surfactant(s) or block copolymer(s) in the SWCCA.

The sorbitan esters or polysorbates can be or replace, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or 100%, of the total weight of the non-ionic surfactants(s) or block copolymer(s) in the SWCCA.

Fabric Conditioning Agent(s)

The SWCCA can contain one or more fabric conditioning agent(s). Fabric conditioning agent(s) can include, for example, one or more quaternary ammonium salts. Fabric conditioning agent(s) can include, for example:

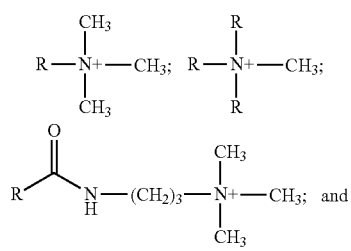

-continued

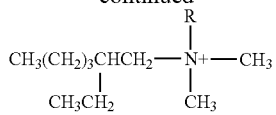

(counterion anion (X$^-$) is present but not shown).

In the structures above, the R group can be, for example, an acyl group. The acyl group can have, for example, a chain that is alkyl, or alkenyl, or alkynyl. The alkyl, alkenyl, or alkynyl chains can be, for example, branched or straight chains, substituted or unsubstituted, cyclic, or optionally interrupted by one or more heteroatoms that can be, for example, oxygen, sulfur, or nitrogen. If the acyl group chain is an alkenyl chain, the chain can contain, for example, one, or two, or three, or four, or five, or six, or seven, or eight, or nine, or more double bonds. If two or more double bonds are present in the alkenyl chain of the acyl group, the double bonds may be, for example, conjugated, not conjugated, or a combination of conjugated and not conjugated. If the acyl group chain is an alkynyl chain, the chain can contain, for example, one, or two, or three, or four, or five, or six, or seven, or eight, or nine, or more triple bonds. If two or more triple bonds are present in the chain of the acyl group, the triple bonds can be, for example, conjugated, not conjugated, or a combination of conjugated and non-conjugated. The acyl group can contain a combination of one or more triple bonds and one or more double bonds.

The acyl group can contain, for example, from 1 to 20 carbon atoms (including the carbon atom of the carbonyl group). Thus, the acyl group can contain, for example, 1 to 15 carbon atoms, 1 to 10 carbon atoms, 1 to 5 carbon atoms, 5 to 20 carbon atoms, 10 to 20 carbon atoms, 15 to 20 carbon atoms, or 5 to 15 carbon atoms (including the carbon atom of the carbonyl group).

The acyl group can contain, for example, the following number of carbon atoms; 1, 2, 3, 4, 5, 6, 7, 8, 9, 10, 11, 12, 13, 14, 15, 16, 17, 18, 19 or 20 carbon atoms (including the carbon atom of the carbonyl group).

In the structures above, the R group can be, for example, an alkyl group, an alkenyl group, or an alkynyl group. The alkyl, alkenyl, or alkynyl groups can be, for example, branched or straight chain, substituted or unsubstitated, cyclic, and optionally interrupted by one or more heteroatoms that can be, for example, oxygen, sulfur, or nitrogen. If the R group is an alkenyl group, the group can contain, for example, one, or two, or three, or four, or five, or six, or seven, or eight, or nine, or more double bonds. If two or more double bonds are present in the alkenyl group, the double bonds may be, for example, conjugated, not conjugated, or a combination of conjugated and not conjugated. If the R group is an alkynyl group, the group can contain, for example, one, or two, or three, or four, or five, or six, or seven, or eight, or nine, or more triple bonds. If two or more tiple bonds are present in the chain of the alkynyl group, the triple bonds can be, for example, conjugated, not conjugated, or a combination of conjugated and non-conjugated. The R group can contain a combination of one or more triple bonds and one or more double bonds.

The alkyl, alkenyl, or alkynyl group(s) can contain, for example, from 1 to 20 carbon atoms. Thus, the groups(s) can contain, for example, 1 to 15 carbon atoms, 1 to 10 carbon atoms, 1 to 5 carbon atoms, 5 to 20 carbon atoms, 10 to 20 carbon atoms, 15 to 20 carbon atoms, or 5 to 15 carbon atoms.

The alkyl, alkenyl, or alkynyl group(s) can contain, for example, the following number of carbon atoms: 1, 2, 3, 4, 5, 6, 7, 8, 9, 10, 11, 12, 13, 14, 15, 16, 17, 18, 19 or 20 carbon atoms.

In anion counterion of the cationic surfactant is not limited. The anion counterion can be, for example, a fluorine anion ($F^-$), a chlorine anion ($Cl^-$), a bromine anion ($Br^-$), or an iodine anion ($I^-$). The anion counter ion can be, for example, a sulfate, a sulfite, a nitrate, a phosphate, a phosphite, a bisulfite, a carbonate, a monohydrogen carbonate, a monohydrogen phosphate, a dihydrogen phosphate, an acetate, a citrate, a lactate, a pyruvate, a silicate, an ascorbate, a nitrite, or any combination thereof. When the anion counterion has a negative charge greater than −1 (e.g., −2, −3), the number of, for example, positively charged ammonium containing molecules are adjusted to balance negative and positive charges.

In some embodiments, the fabric conditioning agent(s) can be, for example, one or more of trimethyltallowamidopropylammonium chloride, trimethylcocalkylamidopropylammonium chloride, trimethylerucylamidopropylammonium chloride, and trimethylhydrogenatedtallowalkylarnidopropylammoniummethosulfate.

In some embodiments, the fabric conditioning agent(s) can be, for example, one or more of ARQUAD 12-35W (AkzoNobel), ARQUAD 16-29 (AkzoNobel), ARQUAD 16-50 (AkzoNobel), ARQUAD 2C-75 (AkzoNobel), ARQUAD 2.10-80 (AkzoNobel), ARQUAD MCB-50 (AkzoNobel), ARQUAD SV-50 (AkzoNobel), ARQUAD SV-60 PG (AkzoNobel), ETHOQUAD C/25 (AkzoNobel), ARMOSOFT TWS-1 (AkzoNobel), or any combination thereof. Preferably, the fabric conditioning agent is one or more of a alkyl trimethyl ammonium compound or an amidopropyl trimethyl ammonium compound, or preferably ARMOSOFT® TWS-1 (AkzoNobel).

The SWCCA can contain fabric conditioning agent(s) in a total amount, for example, ranging from about 10% by weight to about 25% by weight, based on the total weight of the SWCCA.

The fabric conditioning agent(s) can be contained in the SWCCA, in a total amount, for example, ranging from about 10% by weight to about 25% by weight, from about 10% by weight to about 20% by weight, from about 10% by weight to about 15% by weight, from about 15% by weight to about 25% by weight, from about 20% by weight to about 25% by weight, from about 10% by weight to about 20% by weight, or from about 15% by weight to about 20% by weight, based on the total weight of the SWCCA.

The fabric conditioning agent(s) can be contained in the SWCCA, in a total amount, for example, of about 10% by weight, about 12% by weight, about 15% by weight, about 16% by weight, about 17% by weight, about 18% by weight, about 19% by weight, about 20% by weight, about 21% by weight, about 22% by weight, about 23% by weight, or about 24% by weight, based on the total weight of the SWCCA.

Plasticizer(s)

The SWCCA, in some embodiments, does not contain a plasticizer,

In some embodiments, the SWCCA contains one or more plasticizers. The one or more plasticizers can be, for example, glyceryl stearate, polyethylene glycol (PEG) 100 stearate, PEG 200 stearate, PEG 300 stearate, PEG 400 stearate, PEG 500 stearate, PEG 600 stearate, PEG 700 stearate, PEG 800 stearate, PEG 900 stearate, PEG 1,000 stearate, PEG 2,000 stearate, PEG 3,000 stearate, PEG 4,000 stearate, PEG 5,000 stearate, PEG 6,000 stearate, PEG 7,000 stearate, PEG 8,000 stearate, PEG 9,000 stearate, PEG 10,000 stearate, acetyltributyl citrate, acetyltriethyl citrate, benzyl benzoate, cellulose acetate phthalate, chlorbutanol, dextrin, dibutyl phthalate, dibutyl secacate, diethyl phthalate, dimethyl phthalate, glycerin, glycerin monostearate, hypromellose phthalate, mannitol, mineral oil an lanolin alcohols, palmitic acid, polyethylene glycol, polyvinyl acetate phthalate, propylene glycol, 2-pyrrolidone, sorbitol, stearic acid, triacetin, tributyl citrate, triethanolamine, and triethyl citrate.

In some embodiments, the one or more plasticizers can be a combination of PEG 100-stearate and glyceryl monostearate. A particular blend of PEG 100-stearate and glyceryl monostearate is HALLSTAR GMS SE/AS.

In some embodiments, the SWCCA can contain, for example, a total amount of one or more plasticizers ranging from about 8% by weight to about 15% by weight, based on the total weight of the SWCCA. The SWCCA can contain one or more plasticizers in a total amount ranging from, for example, about 8% by weight to about 15% by weight, about 9% by weight to about 15% by weight, from about 10% by weight to about 15% by weight, from about 11% by weight to about 15% by weight, from about 12% by weight to about 15% by weight, from about 13% by weight to about 15% by weight, from about 8% by weight to about 13% by weight, from about 8% by weight to about 10% by weight, or from about 9% by weight to about 13% by weight, based on the total weight of the SWCCA.

The SWCCA can contain, for example, a total amount of one or more plasticizers n of about 8% by weight, about 9% by weight, about 10% by weight, about 11% by weight, about 12% by weight, about 13% by weight about 14% by weight, or about 15% by weight, based on the total weight of the SWCCA.

Colorants

In some embodiments, the SWCCA does not contain a colorant.

In some embodiments, the SWCCA contains one or more colorants.

The colorant(s) can be, for example, polymers.

The colorant(s) can be, for example, dyes.

The colorant(s) can be, for example, water-soluble polymeric colorants.

The colorant(s) can be, for example, water-soluble dyes.

The colorant(s) can be, for example, colorants that are well-known in the art or commercially available from dye or chemical manufacturers.

The color of the colorant(s) is not limited, and can be, for example, red, orange, yellow, blue, indigo, violet, or any combination thereof.

The colorant(s) can be, for example, one or more Milliken LIQUITINT colorants. The colorant(s) can be, for example Milliken LIQUITINT: VIOLET LS, ROYAL MC, BLUE HP, BLUE MC, AQUAMARINE, GREEN HMC, BRIGHT YELLOW, YELLOW LP, YELLOW BL, BRILLIANT ORAGNE, CRIMSON, RED MX, PINK AL, RED BL, RED ST, or any combination thereof.

The colorant(s) can be, for example, one or more of Acid Blue 80, Acid Red 52, and Acid Violet 48.

Acid Blue 48 has the chemical structure:

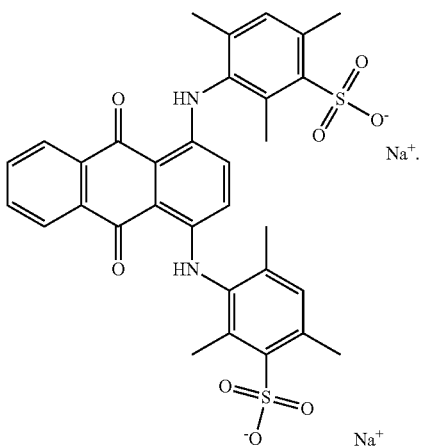

Acid Red 52 has the chemical structure:

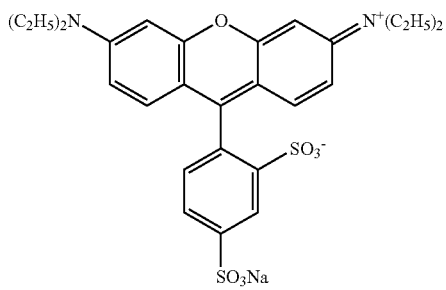

Acid Violet 48 has the chemical structure:

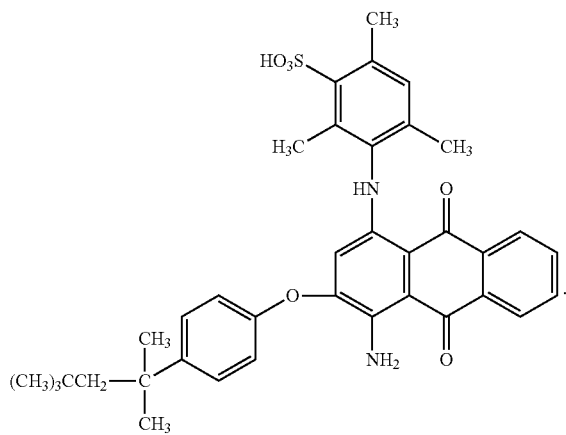

When the colorant(s) are selected from the group consisting of Acid Blue 80, Acid Red 52, and Acid Violet 48, the SWCCA, optionally, does not contain a colorant stabilizer. Surprisingly, it has been found that Acid Blue 80, Acid Red 52, and Acid Violet 48, do not display significant discoloration over time, and thus, can be used without (e.g., in the absence of) a colorant stabilizer.

The total amount of the one or more colorant(s) that can be contained in the SWCCA, for example, can range from about 0.00001% by weight to about 0.099% by weight, based on the total weight of the SWCCA. The total amount of colorant(s) in the SWCCA can be, for example, about 0.0001% by weight, about 0.001% by weight, about 0.01% by weight, about 0.05% by weight, or about 0.08% by weight, based on the total weight of the SWCCA.

Colorant Stabilizer(s)

In some embodiments, the SWCCA can optionally contain a colorant stabilizer. Colorant stabilizers have been disclosed herein. In some embodiments, the colorant stabilizer can be citric acid.

The total amount of the optionally present colorant stabilizer(s) in the SWCCA can range, for example, from about 0.01% by weight to about 5.0% by weight, based on the total weight of the SWCCA. The total amount of the colorant stabilizer(s) in the SWCCA can be, for example, about 0.1% by weight, about 1% by weight, about 2% by weight, about 3% by weight, or about 4% by weight, based on the total weight of the SWCCA.

Perfume(s)

The SWCCA can optionally contain one or more perfumes. Some of all of the one or more perfumes can be optionally encapsulated, for example, in a microcapsule or a nanocapsule. Suitable perfumes are disclosed herein, and are well-known to those of ordinary skill in the art, and are available commercially from a variety of sources such as Firmenich, Givaudan, International Flavors and Fragrances (IFF), Oriental, and the like.

The total amount of the optionally present perfume(s) in the SWCCA can range, for example, from about 0.10% by weight to about 10.0% by weight, based on the total weight of the SWCCA. The total amount of the perfume(s) can be, for example, about 0.5% by weight, about 1% by weight, about 2% by weight, about 4% by weight, about 6% by weight, or about 8% by weight, based on the total weight of the SWCCA.

Other Ingredient(s)

The SWCCA can optionally contain other ingredient(s) as disclosed herein. Some optional ingredients can be, for example, U.S. powdered sugar 10x, DISINTEX 75, polyvinylpyrrolidone K15, sodium sulfate, and sodium chloride.

Forms

The form of the SWCCA is not limited, and can be for example, a powder, a pulverized powder, a tablet, a pastille, or crystalline (e.g., crystal(s)). The SWCCA can be in the form of a unit dose which can be, for example, a tablet. As tablet size increases to a certain point, there becomes a need for including a disintegrant. The disintegrant can be one or more known disintegrants. The disintegrant can be, for example, one or more of hydroxypropyl starch, lactose, corn starch, alginic acid, calcium alginate, carboxymethylcellulose calcium, carboxymethylcellulose sodium, cellulose, cellulose powdered, chitosan, colloidal silicon dioxide, corn starch and pregelatinized starch, croscarmellose sodium, crospovidone, docusate sodium, glycine, guar gum, low-substituted hydroxypropyl cellulose, magnesium aluminum silicate, methyl cellulose, microcrystalline cellulose, polacrilin potassium, povidone, sodium alginate, sodium starch glycolate, pregelatinized starch, DISINTEX 75, or any combination thereof. Disintegrant(s) can optionally be present in the SWCCA, for example, in a total amount ranging from about 0.1% by weight to about 10% by weight, based on the total weight of the SWCCA. The total amount of disintegrant(s) in the SWCCA can be, for example, about 1% by weight, about 3% by weight, about 5% by weight, about 7% by weight, or about 9% by weight, based on the total weight of the SWCCA. Pastilles or crystals or powders or tablets can, for example, be combined together. The combinations can, for example, contain pastilles or crystals or powders or tablets that have the same ingredients in the same amounts, or can, for example, contain different ingredients, or different amounts of the same ingredients. The SWCCAs can be included with detergent(s) to form cleaning agent compositions. Cleaning agent compositions are disclosed herein, and SWCCAs can replace or augment STTCs in cleaning agent compositions.

Methods of Use

The SWCCAs can be used to treat textiles (i.e., to impart scent or soften or clean or decrease static build up when the treated textile is subsequently dried). The SWCCAs can be used in a top loading or front loading washer. The SWCCAs can be used in hot, warm, or cold water. The SWCCAs can be used with a detergent in a wash cycle, or separately but in conjunction with a detergent (e.g., in a separate wash or rinse cycle). The SWCCAs can be used in cleaning agent compositions. The textiles treated with the SWCCAs (or STTCs) can, optionally, be in need of treatment.

Methods of Making SWCCAs

The SWCCAs can be made by any known method. The SWCCAs can be made, for example, by heating the non-ionic surfactant(s) (optionally in the presence of one or two or three or four or five or all of the ingredients in the SWCCA) until the non-ionic surfactant(s) melt and then adding and/or mixing the additional ingredients.

In some embodiments, the non-ionic surfactant(s) are blended with the fabric conditioning agent(s) and the plasticizer(s), heated to form a melt, and optionally mixed. Then, additional ingredients such as colorant(s), colorant stabilizer(s), or fragrance(s) are optionally added and blended. The blends are allowed to cool. Optionally, the heated blends are added repeatedly in small portions as drops to a polymeric film and then allowed to cool and optionally removed from the polymeric film, thereby forming pastilles.

In some embodiments, the SWCCAs can be in the form of tablets, which can be unit doses. To make these, for example, the ingredients in the SWCCAs are blended together, for example, at room temperature, and compressed to form tablets. For larger tablets, it is preferred to add a disintegrant to the mixture of ingredients prior to compressing the mixture into tablets. The blends can be, for example, dry powder blends.

The tableting can occur using any known tablet press, for example, a rotary tablet press. The tableting compression force can range, for example, from about 1,000 pounds to about 15,000 pounds. The tableting compression force can be, for example, about 2,000 pounds, about 3,000 pounds, about 4,000 pounds, about 5,000 pounds, about 6,000 pounds, about 7,000 pounds, about 8,000 pounds, about 9,000 pounds, about 10,000 pounds, about 11,000 pounds, about 12,000 pounds, about 13,000 pounds, or about 14,000 pounds.

Unit Doses

In some embodiments, any of the ingredients listed herein can be combined and compressed, in any way disclosed herein, for forming a unit dose such as the single-chamber unit dose product formats described herein.

A representative unit dose formulation can be, for example: 25% by weight powdered sugar 10×; 3.76% by weight polymer LR400, 1% by weight sodium stearate, 1% by weight DISINTEX 75, 3% by weight PVP-K15, 62.05% by weight sodium sulfate, 4.18% by weight perfume, and 0.001% by weight Acid Blue 80, based on the total weight of the formulation. The unit dose can contain, for example, about 10 g to about 20 g, or about 12 g, or about 14 g, or about 16 g, or about 17 g, or about 19 g, of its formulation.

Another representative unit dose formulation can be, for example, about 94% by weight solar salt with YPS (Morton), about 3.08% by weight High Five ACM 190991 F fragrance (Firmenich), about 0.77% by weight Super Soft Pop 190870 fragrance (Firmenich), about 0.005% Acid Blue 80 dye, and about 1.75% by weight Zeofree® 5161 flow aid (Huber).

Another representative unit dose formulation can be, for example, about 91% by weight solar salt with YPS (Morton), about 2.91% by weight High Five ACM 190991 F fragrance (Firmenich), about 0.73% by weight Super Soft Pop 190870 fragrance (Firmenich), about 0.004% Acid Blue 80 dye, about 2.84% by weight Zeofree® 5161 flow aid (Huber), and about 2.4% by weight water.

Liquid Textile Treating Compositions ("LTTCs")

In some embodiments is provided liquid textile treating compositions ("LTTCs").

The LTTCs can comprise, for example, one or more polyethylene glycols ("PEGs"), one or more alcohols, one or more fabric conditioning agents, water, optionally one or more colorants, and optionally one or more perfumes.

PEG(s)

PEGs are disclosed herein. The one or more PEGs are not limited, and can be, for example, PEG 100, PEG 200, PEG 300, PEG 400, PEG 500, PEG 600, PEG 700, PEG 800, PEG 900, PEG 1,000, PEG 2,000, PEG 3,000, PEG 4,000, PEG 5,000, PEG 6,000, PEG 7,000, PEG 8,000, PEG 9,000, or PEG 1,000.

The total amount of the one or more PEGs contained in the LTTC, for example, can range from about 65% by weight to about 80% by weight, based on the total weight of the LTTC. The total amount of the one or more PEGs can be, for example, about 66% by weight, about 67% by weight, about 68% by weight, about 69% by weight, about 70% by weight, about 71% by weight, about 72% by weight, about 73% by weight, about 74% by weight, about 75% by weight, about 76% by weight, about 77% by weight, about 78% by weight, or about 79% by weight, based on the total weight of the LTTC.

Alcohol(s)

The LTTCs can comprise, for example, one or more alcohols. The one or more alcohols can be, for example, one or more polyols. The one or more polyols can be, for example, glycerol, xylitol, D-xylose, L-xylose, erythritol, maltitol, mannitol, sorbitol, or any combination thereof.

The LTTCs can contain a total amount of the one or more alcohols, for example, in a total amount ranging from about 1% by weight to about 5% by weight, based on the total weight of the LTTC. The total amount of the one or more alcohols can be, for example, about 1.5% by weight, about 2% by weight, about 2.5% by weight, about 3% by weight, about 3.5% by weight, about 4% by weight, about 4.5% by weight, or about 5% by weight, based on the total weight of the LTTC.

Water

The LTTC can contain water, for example, in a total amount ranging from about 5% by weight to about 12% by weight, based on the total weight of the LTTC. The total amount of the water can be, for example, about 5% by weight, about 5.5% by weight, about 6.0% by weight, about 6.5% by weight, about 7% by weight, about 7.5% by weight, about 8% by weight, about 8.5% by weight, about 9% by weight, about 9.5% by weight, about 10% by weight, about 10.5% by weight, about 11% by weight, or about 11.5% by weight, based on the total weight of the LTTC.

Fabric Conditioning Agent(s)

The LTTC can contain, for example, one or more fabric conditioning agents as disclosed herein. The total amount of the fabric conditioning agents can range, for example, from about ranging from about 10% by weight to about 25% by weight, based on the total weight of the LTTC.

The fabric conditioning agent(s) can be contained in the LTTC, in a total amount, for example, ranging from about 10% by weight to about 25% by weight, from about 10% by weight to about 20% by weight, from about 10% by weight to about 15% by weight, from about 15% by weight to about 25% by weight, from about 20% by weight to about 25% by weight, from about 10% by weight to about 20% by weight, or from about 15% by weight to about 20% by weight, based on the total weight of the LTTC.

The fabric conditioning agents(s) can be contained in the LTTC, in a total amount, for example, of about 10% by weight, about 12% by weight, about 15% by weight, about 16% by weight, about 17% by weight, about 18% by weight, about 19% by weight, about 20% by weight, about 21% by weight, about 22% by weight, about 23% by weight, or about 24% by weight, based on the total weight of the LTTC.

The fabric conditioning agents can include cationic surfactants or polymers or fabric softeners as described above.

Colorant(s)

The LTTCs can optionally contain one or more colorant(s) as disclosed herein. The total amount of the one or more colorant(s) that can be contained in the LTTC, for example, can range from about 0.0005% by weight to about 0.0100% by weight, based on the total weight of the LTTC.

Colorant Stabilizers

In some embodiments, the LTTCs can optionally contain one or more colorant stabilizers as disclosed herein. In some embodiments, the colorant stabilizer can be citric acid.

The total amount of the optionally present colorant stabilizer(s) in the LTTC can range, for example, from about 0.0005% by weight to about 0.25% by weight, based on the total weight of the LTTC.

Perfume(s)

In some embodiments, the LTTCs can optionally contain one or more perfumes as disclosed herein and as are known to those of ordinary skill in the art. Some of all of the one or more perfumes can be optionally encapsulated, for example, in a microcapsule or a nanocapsule.

The total amount of the optionally present perfume(s) in the LTTCs can range, for example, from about 3.500% by weight to about 11.00% by weight, based on the total weight of the LTTCs.

Other Ingredient(s)

The LTTCs can optionally contain other ingredient(s) as disclosed herein. The total amount of the optionally present other ingredients(s) in the LTTCs can range, for example, from about 0.0120% by weight to about 0.2500% by weight, based on the total weight of the LTTCs.

Methods of Use

The LTTCs can be used to treat textiles (i.e., to impart scent or soften or clean or decrease static build up while subsequently drying). The LTTCs can be used in a top loading or front loading washer. The LTTCs can be used in hot, warm, or cold water. The LTTCs can be used with a detergent, or separately but in conjunction with a detergent (e.g., in a separate wash or rinse cycle. The LTTCs can be used in cleaning agent compositions. The textiles treated by LTTCs, or cleaning agent compositions containing LTTCs, can optionally be in need of treatment.

Methods of Making LTTCs

The LTTCs can be made by any known method. The LTTCs can be made, for example, by optionally heating and mixing alcohol(s), the PEG(s), the fabric conditioning agent(s), and the water. After mixing, for example, at room temperature, or optionally, with heat, for example, at 60, 70, 80, 90, or 100 degrees F., any remaining ingredients (e.g., perfume(s), colorant(s)) are added with mixing. The resulting LTTC is then allowed to cool to room temperature.

Treated Textiles

In one inventive embodiment is provided a textile treated by an STTC or an SWCCA or an LTTC.

The act of treating a textile can refer to, or example, one or more of: i) applying a perfume to a textile; ii) softening a textile; iii) applying a perfume to and softening a textile; iv) cleaning a textile; v) rendering the textile resistant to static build up during drying; or vi) cleaning a textile and applying a perfume to and softening a textile and rendering the textile resistant to static build up during drying; or any combination thereof.

When rendering a textile resistant to static buildup (e.g., reducing static (electricity) during subsequent drying of the treated textile), treatment of the textile can decrease the number of nano coulombs of charge built up during drying, relative to an untreated control textile, by an amount ranging, for example, from about 40% to about 80%. The amount of reduction can be, for example, about 45%, about 50%, about 55%, about 60%, about 65%, about 70%, or about 75%.

The textile, after being treated, may be further processed, for example by drying, pressing, ironing, steaming, sewing, and the like.

The textile can be in need of treating.

The following examples are illustrative and do not limit the scope of the disclosure of the claims.

EXAMPLES

Example 1

Formation of a Perfume Containing Solid Textile-Treating Composition 13 g of polyethylene glycol 8000 ("PEG 8000") were melted in a heated container equipped with a stirring apparatus. 0.25 g of citric acid, 2.25 g of perfume (Mayflowers TD 485531 EB (Firmenich)), and 0.00650 g of Milliken Liquitint® Royal MC colorant were added to the melted PEG 8000, with stirring, to create a homogenously mixed molten coating mixture.

The molten coating mixture was poured onto 79.494 g of Kleer Salt (Morton) granules. The salt granules and melted coating mixture were agitated, thereby producing coated salt granules.

The coated salt granules were then cooled such that the coating remained tacky, and the 5.00 g of sodium sulfate powder were applied to the exterior coating surface of the coated granules to produce a solid textile-treating composition.

Example 2

Formation of a Perfume and Fabric Softener Containing Solid Textile-Treating Composition 13 g of polyethylene glycol 8000 ("PEG 8000") were melted in a heated container equipped with a stirring apparatus. 0.25 g of citric acid, 2.40 g of perfume (High Five ACM 190991 (Firmenich)), and 0.00650 g of Milliken Liquitint® Royal MC colorant were added to the melted PEG 8000, with stirring, to create a homogenously mixed molten coating mixture.

The molten coating mixture was poured onto 79.354 g of pretzel salt (Morton) granules. The salt granules and melted coating mixture were agitated, thereby producing coated salt granules.

The coated salt granules were then cooled such that the coating remained tacky, and the 2.75 g of sodium sulfate and 2.24 grams of the cationic polymer UCARE LR-400, a cationic HEC polymer, were applied to the exterior coating surface of the coated granules to produce a solid textile-treating composition.

Example 3

Formation of an SWCCA in the Form of Pastilles

A block copolymer (PLURONIC F-38) was mixed with a faLric condition agent (ARMOSOFT TWS-1) and a plasticizer mixture (glyceryl monostearate and PEG-100 monostearate) and the mixture was heated to about 133° F. The mixture melted. A colorant and a perfume were added to the melted mixture, mixing is effected, and the mixture was then dropped repeatedly in small portions onto a polymeric film to form drops. The drops were hardened to form pastilles, which were then removed from the polymeric film. The amounts of ingredients blended together (Formulae 1-3) are presented in the table, below (QA means quality adjusted with color and fragrance to make 100% by weight of the formula):

| Chemical Name | Formula # 1 Ingredients % | Formula # 2 Ingredients % | Formula # 3 Ingredients % |
|---|---|---|---|
| PLURONIC F-38 EO/PO | 73.6 | 68.45 | 63.45 |
| ARMOSOFT TWS-1(85%) | 9.85 | 15 | 20 |
| GMS SE/AS | 13 | 13 | 13 |
| Colorant | QA | QA | QA |
| Perfume | QA | QA | QA |

Example 4

Formation of LTTCs

Polyethylene glycol 200, glycerin, and ARMOSOFT TWS-1 were mixed together with heating. After approximately 10 minutes, water, a colorant, and a perfume were added. The resulting solutions were allowed to cool to room temperature. The contents of the LTTC formulations are presented in the table, below (QA means quality adjusted with color and fragrance to make 100% by weight of the formula):

| Chemical Name | Formula #1 Ingredients % | Formula # 2 Ingredients % | Formula # 3 Ingredients % |
|---|---|---|---|
| Polyethylene Glycol 200 | 74.34 | 74.34 | 74.34 |
| Glycerin | 2.5 | 2.5 | 2.5 |
| ARMOSOFT TWS-1(85% Active) | 9.85 | 15 | 20 |
| Water | 8 | 8 | 8 |
| Colorant | QA | QA | QA |
| Perfume | QA | QA | QA |

Example 5

Preparation of Unit Dose Tablets and Solubility Testing Thereof

Unit dose tablets were prepared by compressing, with 9000 pounds of force, the following ingredients, to form the tablets:

| Component | % Formula (by weight) |
|---|---|
| U.S. Powdered Sugar 10 x | 25.00 |
| Polymer LR-400 | 3.76 |
| Sodium Stearate P-100V | 1.00 |
| Disintex 75 | 1.00 |
| Polyvinylpyrrolidone-K15 | 3.00 |
| Sodium sulfate powder | 62.052 |
| Mayflowers TD190832F | 4.18 |
| Acid Blue 80 (12% premix with polypropylene glycol) | 0.08 .001% pure dye) |

24 Tablets in total were made. Each tablet weight about 17 g.

A representative tablet was tested for ability to dissolve in water as follows: a 17 gram tablet was placed in 700 g of water having a temperature of 68 degrees F. The tablet dissolved in 2 minutes and 15 seconds.

Example 6

Preparation of Unit Dose Solid Fragrance Boosters

Unit dose packets of fragrance booster STTCs were prepared by mixing the following ingredients:

| Component | % Formula (by weight) |
|---|---|
| Solar salt with YPS | 91.1 |
| Zeofree® 5161 | 2.84 |
| High Five ACM 190991 F | 2.91 |
| Super Soft Pop 190870 | 0.728 |
| Water | 2.37 |
| Acid Blue 80 (12% premix with polypropylene glycol) | 0.00429 |

In a related formulation, unit dose packets of fragrance booster were prepared by mixing the following ingredients:

| Component | % Formula (by weight) |
|---|---|
| Solar salt with YPS | 94.4 |
| Zeofree® 5161 | 1.75 |
| High Five ACM 190991 F | 3.077 |
| Super Soft Pop 190870 | 0.769 |
| Acid Blue 80 (12% premix with polypropylene glycol) | 0.00450 |

Following formulation, the fragrance delivery STTCs were packaged into single-chamber PVOH film packets using the Cloud machinery and methodology as described elsewhere herein. In related such embodiments, the fragrance delivery STTCs were included in unit dose containers also containing detergent-containing formulations. These unit dose STTCs are suitable for delivery of fragrance to fabrics by including the unit dose STTCs with the clothing in the wash chamber at the beginning of the wash cycle.

Example 7

Testing for the Ability to Soften Textiles

A Phabrometer Instrument, manufactured by Nucybertek, was employed to test to softening ability.

12 knitted cotton replicate fabric pieces (disc shaped) were created from 4 independent fabric swatches. Five pounds of ballast were included for each wash of the swatches. The swatches (3 reps per fabric swatch) and ballast were washed in cells using All Free Clear detergent. ARMOSOFT-TWS-1 containing formulations were added to the wash cycle of cells 1-3 but not added to cell 4 (control cell). Terry towels were also included in the wash cells for subjective testing.

The following is the amount of ARMOSOFT-TWS-1 in the formulations in % by weight, based on the total weight of the formulations:

| Cell # | Weight % ARMOSOFT-TWS-1 in Formulation | Formulation Designation |
|---|---|---|
| 1 | 9.85% by weight | CR1-105-EX |
| 2 | 15% by weight | CR1-136-EX |
| 3 | 20% by weight | CR1-1237-EX |
| 4 | Untreated | Untreated |

The settings for each cell were as follows:

| Settings |
|---|
| Water Hardness—150 ppm |
| Water Temperature—90 degrees F. |
| Dosages 32.21 g of formulation, where applicable |
| Wash Cycle—14 minutes |
| Water Level—18 gallons |

After each run, the washed towels were dried for 60 minutes. The dry swatches were evaluated in the Phabrometer by being individually weighed down and forced through an orifice while measuring and/or calculating hand attributes (e.g., softness).

Response softness was found to be as follows base on weight % of ARMOSOFT-TWS-1 in the formulation:

| Active Level | Letter Designation | Letter Designation | Letter Designation | Least Square Mean |
|---|---|---|---|---|
| 20% by wt. | A | | | 6.51 |
| 15% by wt. | A | B | | 6.43 |
| untreated | | B | C | 6.31 |
| 10% by wt. | | | C | 6.29 |

Levels not connected by the same letter are significantly different.

The results indicate that 20% inclusion of ARMOSOFT-TWS-1 showed a statistically difference in softening as perceived by the Phabrometer. The 15% inclusion level showed a trend of improved softening but was not statistically different than untreated. The 10% inclusion level did not show any softening response by the Phabrometer.

All publications, patents, and patent applications mentioned herein are incorporated by reference in their entireties.

What is claimed is:

1. A unit dose solid textile-treating article, comprising:
   a water-soluble single-chamber container; and
   at least one solid textile-treating composition, which comprises:
   (a) a water-soluble core comprising a water-soluble carrier;
      wherein the water-soluble core is in particle form having an average particle size from about 0.1 mm to about 50 mm;
   (b) a coating that at least partially covers the water-soluble core, the coating comprising:
      (i) a water-soluble polymer;
      (ii) a colorant; and
      (iii) a colorant stabilizer that is an acid having a molecular weight of 1000 daltons or less;
      wherein the colorant stabilizer is formic acid, an acetic acid, a propanoic acid, a butanoic acid, a pentanoic acid, a hexanoic acid, a heptanoic acid, a octanoic acid, a nonanoic acid, a decanoic acid, a cyclopropyl carboxylic acid, a cyclobutyl carboxylic acid, a cyclopentyl carboxylic acid, a cyclohexyl carboxylic acid, a cycloheptyl carboxylic acid, a cyclooctyl carboxylic acid, a cyclononylcarboxylic acid, a cyclodecanoyl carboxylic acid, a lactic acid, a pyruvic acid, a phenol, or a combination thereof; and
   (c) a flow aid mixed into the coating such that the flow aid is partially or fully exposed on an outer surface of the coating;
      wherein the at least one solid textile-treating composition does not contain a polysaccharide;
      wherein the water-soluble single-chamber container contains the at least one solid textile-treating composition.

2. The unit dose solid textile-treating article of claim 1, wherein said single-chamber container is a formed, sealed pouch produced from a water-soluble polymer or film.

3. The unit dose solid textile-treating article of claim 1, wherein the coating further comprises a perfume.

4. The unit dose solid textile-treating article of claim 3, wherein said water-soluble carrier comprises solar salt with yellow prussiate of soda.

5. The unit dose solid textile-treating article of claim 3, wherein the unit dose solid textile-treating article further comprises water.

6. The unit dose solid textile-treating article of claim 3, wherein at least some of the perfume is encapsulated.

7. The unit dose solid textile-treating article of claim 6, wherein at least some of the encapsulated perfume is encapsulated in a microcapsule.

8. The unit dose solid textile-treating article of claim 1, wherein the coating does not comprise a perfume.

9. The unit dose solid textile-treating article of claim 1, wherein the flow aid comprises a fabric softener.

10. The unit dose solid textile-treating article of claim 9, wherein the fabric softener is a polysiloxane, a textile-softening clay, a cationic polymer, or any combination thereof.

11. The unit dose solid textile-treating article of claim 1, wherein the water-soluble carrier is sodium chloride, potassium chloride, calcium chloride, magnesium chloride, sodium sulfate, potassium sulfate, magnesium sulfate, sodium carbonate, potassium carbonate, sodium hydrogen carbonate, potassium hydrogen carbonate, sodium acetate, potassium acetate, sodium citrate, potassium citrate, sodium tartrate, potassium tartrate, potassium sodium tartrate, calcium lactate, water glass, sodium silicate, potassium silicate, dextrose, fructose, galactose, isoglucose, glucose, sucrose, raffinose, isomalt, xylitol, candy sugar, coarse sugar, or any combination thereof.

12. The unit dose solid textile-treating article of claim 1, wherein the coating completely surrounds the water-soluble core.

13. The unit dose of solid textile-treating article of claim 1, wherein the water-soluble polymer is a polyalkylene glycol, a polyethylene glycol, a polyethylene terephthalate, a polyvinyl alcohol, or any mixture thereof.

14. The unit dose solid textile-treating article of claim 1, wherein the colorant in the composition changes hue or becomes substantially colorless in the absence of the colorant stabilizer after a time period ranging from about 2 weeks to about 3 months.

15. A unit dose solid textile-treating article, comprising:
a water-soluble single-chamber container; and
at least one solid textile-treating composition, which comprises:
 (a) a water-soluble core comprising a water-soluble carrier;
  wherein the water-soluble core is in particle form having an average particle size from about 0.1 mm to about 50 mm;
 (b) a coating that at least partially covers the water-soluble core, the coating comprising:
  (i) a water-soluble polymer;
  (ii) a colorant; and
  (iii) a colorant stabilizer having a molecular weight of 1000 daltons or less;
 (c) a flow aid mixed into the coating such that the flow aid is partially or fully exposed on an outer surface of the coating;
  wherein the colorant stabilizer is an alkyl carboxylic acid, a cycloalkyl carboxylic acid, heterocycloalkyl carboxylic acid, an aryl carboxylic acid, heteroaryl carboxylic acid, a cycloalkyl alkyl carboxylic acid, an aryl alkyl carboxylic acid, a heterocycloalkyl alkyl carboxylic acid, a heteroaryl alkyl carboxylic acid, or any combination thereof;
 wherein the at least one solid textile-treating composition does not contain a polysaccharide;
 wherein the water-soluble single-chamber container contains the at least one solid textile-treating composition.

16. The unit dose solid textile-treating article of claim 1, wherein the flow aid comprises an inorganic alkali metal salt, an inorganic alkaline earth metal salt, a silicate, an aluminosilicate, an amorphous silica, or any combination thereof.

17. A method of delivering a fragrance to a fabric, comprising contacting said fabric with the unit dose textile-treating article of claim 3 in a wash cycle, and drying said fabric.

* * * * *